United States Patent
Yeck et al.

(10) Patent No.: US 9,792,548 B2
(45) Date of Patent: Oct. 17, 2017

(54) SYSTEMS AND METHODS FOR BIOCHEMICAL DATA ANALYSIS

(71) Applicant: Bio-Rad Laboratories, Inc., Hercules, CA (US)

(72) Inventors: Todd Yeck, Sausalito, CA (US); Niels Kirk Thomsen, Santa Rosa, CA (US); John Clopton Dunaway, Walnut Creek, CA (US)

(73) Assignee: Bio-Rad Laboratories, Inc., Hercules, CA (US)

( * ) Notice: Subject to any disclaimer, the term of this patent is extended or adjusted under 35 U.S.C. 154(b) by 746 days.

(21) Appl. No.: 13/625,753

(22) Filed: Sep. 24, 2012

(65) Prior Publication Data

US 2013/0080373 A1    Mar. 28, 2013

Related U.S. Application Data

(60) Provisional application No. 61/538,073, filed on Sep. 22, 2011.

(51) Int. Cl.
| | | |
|---|---|---|
| *G06N 5/02* | (2006.01) | |
| *G06F 19/26* | (2011.01) | |
| *G06F 19/28* | (2011.01) | |

(52) U.S. Cl.
CPC .............. *G06N 5/02* (2013.01); *G06F 19/26* (2013.01); *G06F 19/28* (2013.01)

(58) Field of Classification Search
None
See application file for complete search history.

(56) References Cited

U.S. PATENT DOCUMENTS

| | | |
|---|---|---|
| 6,683,455 B2 | 1/2004 | Ebbels et al. |
| 7,901,873 B2 | 3/2011 | Nicholson et al. |
| 2002/0045808 A1* | 4/2002 | Ford et al. ................ 600/347 |
| 2004/0080536 A1* | 4/2004 | Yakhini et al. ............ 345/764 |
| 2005/0155037 A1 | 7/2005 | Klein et al. |
| 2006/0004530 A1 | 1/2006 | Miyamoto et al. |
| 2008/0263468 A1* | 10/2008 | Cappione et al. ........... 715/771 |
| 2009/0024940 A1* | 1/2009 | Zeringue et al. ........... 715/763 |
| 2009/0106185 A1 | 4/2009 | Buhl et al. |
| 2009/0248443 A1* | 10/2009 | Kelly et al. .................... 705/3 |
| 2009/0307527 A1* | 12/2009 | Robbins et al. .............. 714/15 |
| 2010/0082634 A1* | 4/2010 | Leban ......................... 707/741 |

FOREIGN PATENT DOCUMENTS

| | | |
|---|---|---|
| CN | 1902587 A | 1/2007 |
| CN | 101079030 A | 11/2007 |
| CN | 101528118 A | 9/2009 |
| JP | 2006-017637 A | 1/2006 |
| JP | 2007-333466 A | 12/2007 |
| JP | 2009-501333 A | 1/2009 |
| JP | 2009-036513 A | 2/2009 |
| JP | 2010-107433 A | 5/2010 |
| JP | 2010-230428 A | 10/2010 |
| WO | 99/13316 A1 | 3/1999 |
| WO | 2011/037069 A1 | 3/2011 |

OTHER PUBLICATIONS

SigmaPlot brochure, 2010.*
International Search Report and Written Opinion dated Dec. 6, 2012, PCT/US12/56939, 7 pages.
Chinese Office Action dated Mar. 24, 2015 for CN Patent Application No. 201280057371.2, with English translation, 16 pages.
Office Action for Japanese Patent Application No. 2014-532077, dated Jun. 21, 2016 with English translation.

* cited by examiner

*Primary Examiner* — Michael Borin
(74) *Attorney, Agent, or Firm* — Kilpatrick Townsend & Stockton LLP

(57) ABSTRACT

Methods and systems for biochemical data analysis are provided. A dataset can be received and a selection of a compare field can be used for creation of sub-groups of data to run statistical analysis on. The sub-groups of the dataset can be created based on the selection of the compare field. Statistical information about each sub-group of data can be calculated and displayed on a user display. Other information can be provided for further dataset refinements. A user may supply a control group selection, and such a selection may then result in an indication on the display of which population represents the control group. A user may supply information for further dataset filtering. Such information may be used to filter data, prior to creating the sub-groups for statistical analysis.

22 Claims, 12 Drawing Sheets

FIG. 11

SYSTEMS AND METHODS FOR BIOCHEMICAL DATA ANALYSIS

CROSS-REFERENCES TO RELATED APPLICATIONS

The present application claims priority from and is a non-provisional application of U.S. Provisional Application No. 61/538,073, entitled "Systems and Methods for Biochemical Data Analysis" filed Sep. 22, 2011, the entire contents of which are herein incorporated by reference for all purposes.

BACKGROUND

The present invention relates generally to biochemical data analysis, and more specifically to analysis of biochemical data using user-supplied parameters.

Biochemical experimental data analysis continues largely in a manual fashion. Users obtain experimental data on research conducted on biological samples, via various empirical means, including results of software program outputs. Such data can be voluminous with a wide variety of characteristics, and consequently cumbersome to manage and analyze. Current users often employ Excel, performing many manual steps for importing data into spreadsheets, for selecting categories of data from the entire dataset for evaluation and comparison, and for providing macros for statistical calculations and charting. Manual solutions are difficult for users to implement and manage, time consuming, error-prone, and a potential business risk.

Users do not currently have an easy to use interface and system for easily providing information about how to slice datasets, resulting in automatic updating of subsets of data, user views of statistical information and/or recalculations of data (e.g. statistics on the data and charts).

Therefore it is desirable to provide systems and methods that overcome the above and other problems.

BRIEF SUMMARY

Embodiments can provide methods and systems for biochemical data analysis. For example, a dataset can be received and a selection of a compare field can be used for creation of sub-groups of data to run statistical analysis on. The sub-groups of the dataset can be created based on the selection of the compare field. Statistical information about each sub-group of data can be calculated and displayed on a user display. In various aspects, other information is provided for further dataset refinements. In one aspect, a user may supply a control group selection. Such a selection may then result in an indication on the display of which population represents the control group. In another aspect, a user may supply information for further dataset filtering. Such information may be used to filter data, prior to creating the sub-groups for statistical analysis.

According to one embodiment, a method of biochemical data analysis is provided. A computer system receives a dataset for a plurality of biological samples. The dataset has a plurality of fields for each biological sample, where at least a portion of the dataset is obtained from experiments involving the biological samples. The dataset includes a plurality of first fields. Each first field includes a plurality of values, each value corresponding to a respective characteristic of a respective biological sample. The dataset also includes one or more second fields. Each second field corresponds to a respective analyte and includes a plurality of concentrations of the respective analyte in the experiments. Each concentration in a respective second field corresponds to a respective biological sample. A selection of a compare field from the plurality of first fields is received. The computer system identifies subgroups of the biological samples in the dataset for statistical analysis based on the plurality of values for the compare field. A subgroup has a same value for the compare field. A selection of an analyte from the one or more second fields for statistical analysis is received. A display of information separated by subgroups is provided to convey statistical information for the selected analyte for each subgroup of the compare field.

Other embodiments are directed to systems, apparatuses, and computer readable media associated with methods described herein.

Reference to the remaining portions of the specification, including the drawings and claims, will realize other features and advantages of the present invention. Further features and advantages of the present invention, as well as the structure and operation of various embodiments of the present invention, are described in detail below with respect to the accompanying drawings. In the drawings, like reference numbers can indicate identical or functionally similar elements.

BRIEF DESCRIPTION OF THE DRAWINGS

In the following drawings like reference numbers are used to refer to like elements. Although the following figures depict various examples of the invention, the invention is not limited to the examples depicted in the figures.

FIG. 11 is a screenshot of a UI page of one embodiment of a biochemical analysis system, illustrating one example of data modification and annotation of the system.

DETAILED DESCRIPTION

Figure 1A:
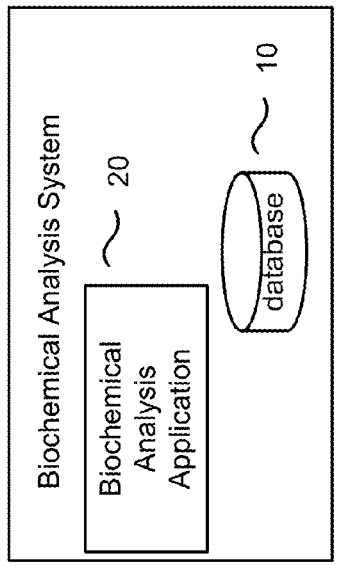
FIG. 1A is a block diagram illustrating a biochemical analysis system running an instance of a biochemical analysis components.

Researchers and other users run various experiments on biological samples (e.g., experiments on blood samples to determine concentrations of various analytes). Such users then may require analysis of data gathered from various experiments. Analysis may be performed by importing data obtained from experiments into a database and analyzing the imported data using a variety of tools. In some cases, users may want to perform statistical analysis on experimental data to gain insight into characteristics of populations of data. As an example, analysis may be performed on polymerase chain reaction (PCR) data or any other data from other biochemical processes.

The following are examples of other data. Immunoassay data may be derived from any platform (e.g., plate-based enzyme-linked immunosorbent assay (ELISAs), multiplex platforms of any flavor including planar arrays, bead based assays, flow cytometry, and other measurement techniques), which can use either raw fluorescence or a calculated concentration derived from a calibration curve. Real time PCR data can use either relative quantity (also known as normalized quantity, or fold expression) or calculated values derived from a calibration curve. Microarray data typically use raw fluorescence values (which may be modified by some background subtraction). Mass spectroscopy data typically use area under peaks. Other data could include pulmonary function data, such as lung function usually measured in volume of air displaced; blood chemistry (e.g. tests for HDL, Cholesterol, Liver enzymes, etc.); and physical measurements, such as bone density, bone length, and circumference of ankle (e.g., to measure swelling in and experimental animal).

The research data may be imported into a database and then analyzed by an application that takes in various user parameters to calculate statistics for the dataset and to provide information to the user about the calculations. Thus, embodiments can provide user-defined parameterization of data, which may be used to divide datasets into subsets of data for statistical analysis. The subsets can be analyzed to provide updated user views of data presentation and/or statistical information by each subgroup of data.

Users can supply certain parameters for statistical analysis. For example, users may provide selections such as compare field, control group, statistical test type, filtering parameter and filtering criteria. A compare field may represent the field by which a researcher is interested in subdividing a dataset for statistical analysis. For a dataset obtained from experiments on a plurality of biological samples containing information about cancer type for each sample, a researcher may be interested in studying the characteristics (e.g. the concentration of a particular analyte, etc.) in sub-populations of each particular cancer type. In that case, a user may select a "disease condition" field as the compare field of choice.

A control group may represent a sub-group or sub-population of data considered as the experimental control. For example, where "disease condition" is selected as a comparison field as discussed above, a data value of "normal" or "healthy individual" may be selected as a control group. Such a group may provide a baseline by which to compare all other sub-populations of a dataset.

Additionally, a researcher may be interested in further filtering of a dataset to gain insight into various characteristics of a dataset. For example, continuing with the above "disease condition" sub-populations example, a research may want to study analyte concentrations for various types of cancers for only male subjects. In such a case, a user may want to provide a compare field selection of "disease condition", which can result in the data for all of the samples for a particular "disease condition" being analyzed and displayed as a group, and data for samples of other "disease conditions" being similarly analyzed and displayed as a group. A user can also select a control group of "normal" (i.e. no disease), and further provide filtering information, such as a gender being equal to "male" only. Other parameters may be user-supplied or system provided for automation of biochemical analysis. The above parameters are provided merely as examples and are not meant to limit the scope of the claimed embodiments.

I. Systems Overview

FIG. 1A is a block diagram illustrating a biochemical analysis system 1 running an instance of a biochemical analysis application. In various embodiments, biochemical analysis system can support user importation of experimental datasets, user selections of various parameters for statistical calculations, and automated calculations and updates of display of statistical information. In one implementation, a database component 10 and a biochemical analysis application 20 runs on a client computer. In another implementation, the database component 10 and a biochemical analysis application 20 are distributed across multiple computers, e.g., in a client-server architecture.

Database component 10 may be used to store and manage experimental datasets, user preferences and inputs, and calculated or analyzed values. Database component 10 may be a relational database, an object-oriented database, or any other suitable database that can support the logic of the biological data analysis system. For example, embodiments may be practiced using database architectures, i.e., ORACLE®, SQLServer®, DB2® by IBM and the like without departing from the scope of the embodiments claimed.

Application 20 can provide a user interface for analysis of data resident in database 10. In one embodiment, the data base can be external to the application 20. In another embodiment, the database can be embedded in the application 20. In yet another embodiment, the application can have an embedded data structure (which may be a database) for processing selected data, and an external database that can persist data across many users, samples, and experiments. Application 20 may be written in any language that can achieve the functionality required for implementing the biochemical analysis system. For example, it may be developed using JAVA, .NET, C, C++, C#, or any other suitable language without departing from the scope of the embodiments claimed.

In various embodiments, database 10 and/or application 20 may run on more than one machine. The system may also work over any network, e.g., the Internet. In one internet implementation, database 10 may reside on a network connected to the internet, and application 20 may reside on another network also connected to the internet. Components 10 and 20 may be distributed in any manner suitable over a networked system without deviating from the scope of the embodiments claimed. In one embodiment, database component 10 may run on one or more separate database machines, to which one or more instances of application 20 may be connected. Users of such a distributed client-server application may connect to the database, e.g., using a dedicated TCP/IP port and assigned database login. In another aspect, internet users may connect to database 10 using an HTTP and/or HTTPS connection.

Figure 1B:
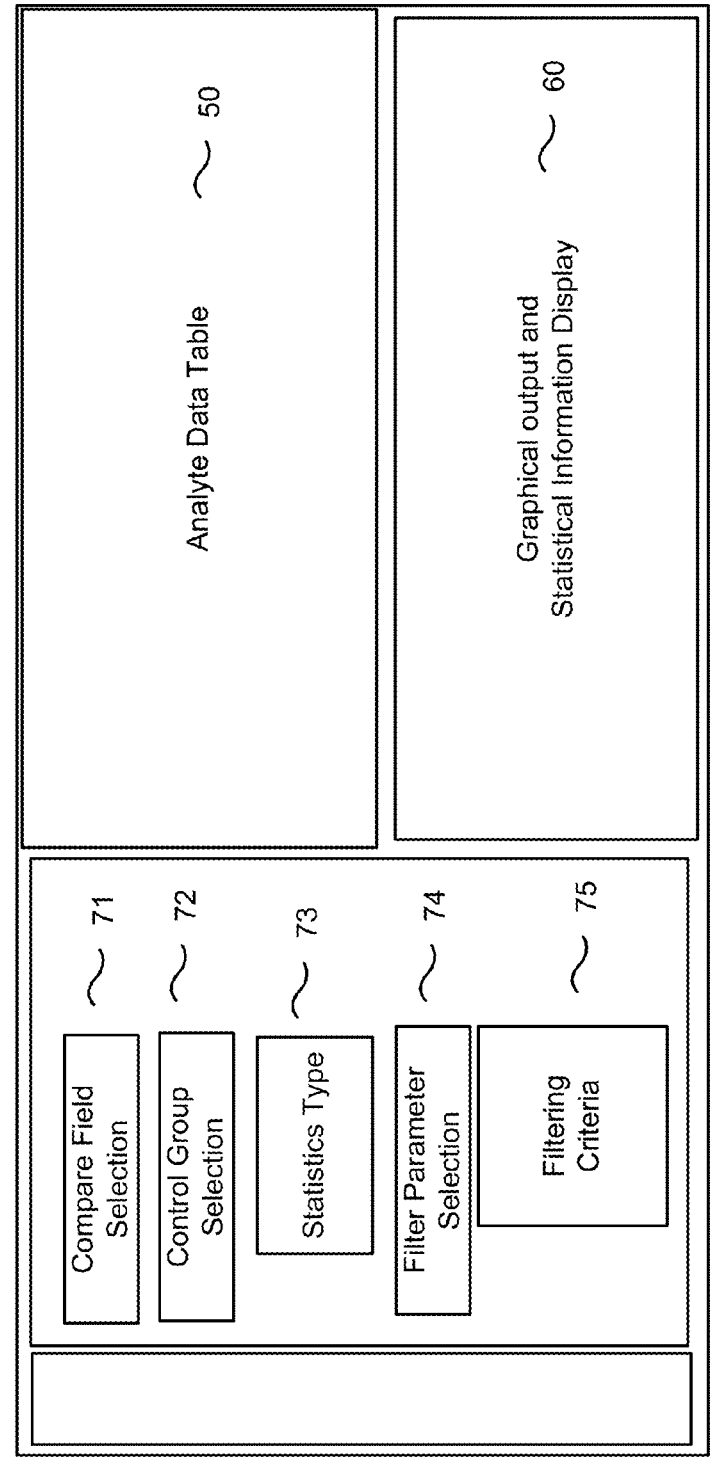
FIG. 1B is a block diagram illustrating various GUI components of an embodiment of biochemical analysis application.

FIG. 1B is a block diagram illustrating various graphical user interface (GUI) components of an embodiment of biochemical analysis application 20. As shown, application 20 includes: Analyte Data Table 50, Graphical Output and Statistical Information Display 60, Compare Field Selection 71, Control Group Selection 72, Statistics Type 73, Filtering Parameter Selection 74, and Filtering Criteria 75. In one aspect Analyte Data Table 50 can be used to display a tabular representation of various analytes and their average concentrations and other calculations. Table 50 may be used to select an analyte of interest for statistical analysis by, e.g., highlighting a row in the analyte table.

Statistical Information Display 60 can display a table of a selected analyte from component 50, and various statistical information in tabular form for a dataset of the selected analyte. Component 60 can also be used to display graphical information about a selected analyte such as scatter plots, bar graphs, box and whisker graphs, etc, which may be presented in series. Statistical Information Display 60 may be used to display any kind of calculated information desired without deviating from the scope of the embodiments.

Application 20 is further shown to include: a Compare Field Selection 71, representing a GUI component by which a user may provide a comparison field for creating sub-populations for statistical analysis; a Control Group Selection 72, representing a GUI component by which a user may provide a control group as the experimental control; a Statistics Type 73 component, representing a GUI component by which a user may provide information about the type of statistical calculations a user is interested in; and a Filter parameter 74 and Filtering Criteria 75 GUI components, representing a mechanism by which a user may provide dataset filtering information.

Various GUI components 71-75 may be implemented as drop-down list boxes by which a user can select a particular parameter of interest. Other GUI components 71-75 may be implemented as input fields, or radio buttons, or checkboxes, or any other suitable selection mechanisms by which a use may supply parameter selection information. GUI components may be arranged in any order, on one page or multiple pages, etc. without deviating from the scope of the claimed embodiments. FIG. 1B illustrates one GUI implementation, but other GUI layouts may be used.

II. Biochemical Data Analysis

Figure 2:
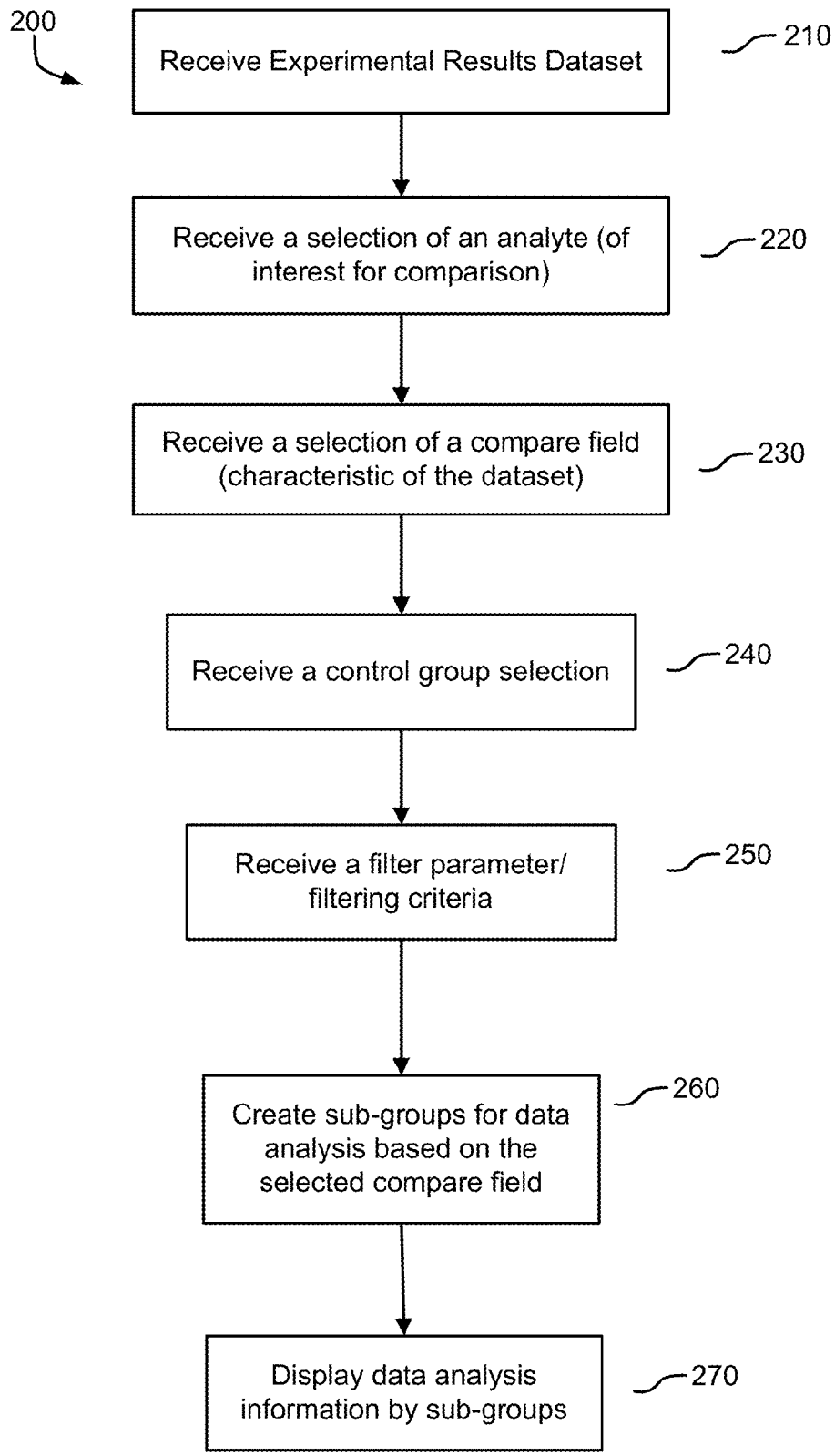
FIG. 2 is a flowchart illustrating the steps for biochemical data analysis system.

FIG. 2 illustrates a method 200 for biochemical data analysis according to embodiments of the present invention. As shown, method 200 includes a receiving of dataset step 210, an analyte selection step 220, compare field selection step 230, a control group selection step 240, a filter parameter/criteria selection step 250, a sub-group creation step 260, and a display of statistical information step 270. These steps may be performed in various orders, in parallel, and one or more steps may optionally not be performed.

In step 210, a system (e.g., as described in FIG. 1A) receives an experimental results dataset for a plurality of biological samples. The samples may be, for example, plasma or serum obtained from human subjects. The biological samples may be obtained from any number of organisms, and any number of biological tissues without deviating from the scope of the claimed embodiments. Examples of sample types include serum, plasma, cell cultures, and different exposure groups.

The dataset may comprise a plurality of data rows, with various attributes (fields) for each data row. Some of the attributes may provide information about the characteristics of the organism form which a biological sample was obtained. In one embodiment, a data row represents a biological sample. For example, one data row may have attributes for gender, age, disease condition, etc. having values in respective fields (e.g., arranged in columns) in the respective row for the corresponding sample. Other data fields (attributes) may contain values obtained from experimentation on the biological samples. For example, a data row may contain various analyte concentrations (e.g., one per concentration field) from one or more experiments performed on the respective biological sample. Thus, each data row may represent one biological sample, with a plurality of fields characterizing the sample and providing values from experimental results, e.g., analyte concentration, florescence intensity (FI), or any other numerical measurement that results from one or more experiments.

Other data rows can correspond to other biological samples. The data rows can values for the same data fields, e.g., all can have a value for a "gender" data field. The data fields may be arranged as columns, where a column corresponds to a particular data field. In one embodiment, more than one data row may be represented by the experimental results for one particular biological sample, e.g., to show results from repeats of a same experiment.

The imported dataset may be associated with a project. For example, one dataset may be imported into a project for "cancer study 1", while another dataset may be imported for "ethnicity variation amongst females study 100". A dataset to project correlation can help in providing varying characteristics of datasets based on the type of study a researcher is performing.

In step 220, the system receives a selection of an analyte for data analysis. For example, a user may provide a selection of an analyte for data analysis. For instance, a user may select a data row representing the average values for a particular analyte in Analyte Data Table 50 of FIG. 1B, which contains data for a plurality of analytes. Any other suitable means for providing the analyte of interest, e.g. inputting the name, selecting from a drop-down box, etc., may be used.

In step 230, the system receives a selection of a compare field. For example, a user may provide a selection of a compare field. A compare field may be selected from one of a plurality of fields for a dataset that characterizes the biological samples. In one implementation, where a data row has attributes for gender, ethnicity, sex, and disease condition, a Compare Field Selection 71 of FIG. 1B may be populated with the illustrative four attributes as possible selections for the compare field. A user could then select one of the four fields as the comparison field of choice. A user may be permitted to select more than one comparison field (e.g., disease condition and gender, resulting in a further division of sub-populations of a dataset by disease and gender). A default compare field value may exist where the user does not provide a selection.

In one embodiment, a drop-down list box for compare field selection may be automatically populated with values corresponding to attributes of a dataset, upon user selection of a dataset for analysis. In another embodiment, a compare field list box may instead contain static values for user selection. The possible comparison fields presented to a user for selection may be constrained by the possible attributes of a dataset. Thus, the system in response to a project having a dataset with two attributes, disease and gender, may make only those two fields available for selection as a compare field.

In step 240, the system receives a selection of a control group, which may be provided by a user. A control group list may include possible data values of the selected comparison field. For example, where disease condition is selected as the comparison field, Control Group Selection 72 of FIG. 1B may be populated with all unique possible values in the disease condition field of a dataset. As such, this may result in a control group list including "lung cancer", "breast cancer", "normal", and "colon cancer". A user may then select any value as the control group, e.g., the "normal" sub-group.

In one implementation, the selection of a compare field in step 230, automatically updates the possible data values for selection of a control group. The automatic update of values in a control group list box may be achieved automatically, e.g., by selecting all unique possible data values for the selected comparison field from the dataset being analyzed and populating the control group list box with the unique values for user selection. In one embodiment, a user may be able to select more than one control group.

The selection of a control group at step 240 may result in a visual indication of the data results display window. For example, the resultant analyzed views (e.g. bar chart, scatter plot, etc.) may have the control group data on the very left of the series of charts or on the very top of a analyzed statistics table. Visual indications of which population represents a control group provide advantages for easy comparison of a control group with other populations in a study. Where the calculated data is exported to a file, the control group may be indicated as either a string or other textual indicator in the export file.

At step 250, the system receives filtering information (e.g., criteria values for filtering parameters), which may be provided by a user. In various embodiments, a user may provide a filtering parameter and filtering criteria for further dataset refinement for analysis purposes. A filtering parameter may be one or more of the attributes or fields for each data row in the dataset being analyzed (e.g., age, gender, ethnicity, disease condition, sample type, etc.). In one embodiment, a filtering parameter component, e.g., Filter Parameter Selection 74 of FIG. 1B, may be automatically populated with possible values of fields of a dataset, upon user selection of the dataset for analysis. In another embodiment, a filter parameter control can contain static values for user selection. The filtering criteria can represent the possible data values of a selected filtering parameter (e.g., male or female where the selected filtering parameter is gender). In one embodiment, a user may be permitted to select more than one filtering criteria for dataset filtering.

In one implementation, once the user selects a filtering parameter, it triggers an automatic update of possible values for selection of filtering criteria. For example, if a user selects sample type as a filtering parameter, a list with check boxes next to it may be updated with the possible data values of "plasma" or "serum", for a Filtering Criteria 75 such as described for FIG. 1B. In one embodiment, a user may then select one or both of the sample type values for statistical analysis. For example, where a user is only interested in looking at the plasma samples values for analysis, she may check only the checkbox next to "plasma".

In step 260, user supplied parameters and criteria are employed to generate sub-groups of data for statistical analysis. In one embodiment, the sub-groups are based on the selected compare field. For example, given a dataset for analysis having 900 total rows of data: with 300 rows having a value of "lung cancer" for a condition column, 300 rows having a value of "colon cancer" for a condition column, and 300 rows having a value of "normal" for a condition column, three different sub-groups may be determined. The actual number of sub-groups and the number of data points per sub-group can depend on filtering parameters and criteria. In the above example, if the 900 rows have a value of "female" for half of the samples in each of the above categories, and a value of "male" for the other half of the data rows for a gender column, then a filter of male might provide 150 data points for each condition. In one implementation, the generation of the sub-groups may be performed automatically and in response to any one of the above selection steps.

In step 270, the data analysis information can be displayed by sub-group. In one embodiment, the data analysis information is calculated each time a new filter, compare field, control, or other relevant value is changed. In one implementation, the calculations are done on-the-fly to reduce storage requirement and provide immediate results to the customer. For example, if the data to be displayed is changed from a fluorescent signal (described in more detail below) to the observed concentration and then back to the fluorescent signal, the calculations for the fluorescent signal would be performed again. Thus, many options exist for the data to be analyzed, the calculations to be performed on the data, and how the data and any calculated values (e.g. statistical values) are to be displayed.

Taking a hypothetical user selection of "condition" as the comparison column, "normal" as the control group, gender as the filter parameter, and "male" as the filtering criteria—first a filtering step of the dataset by "male" and then a sub-grouping of data step may be performed. The resulting sub-groups for analysis would then be: "lung cancer", "colon cancer", and "normal", marking the "normal" category with a flag as the control group. In the example, this would then result in analyzing 150 rows of data, as a result of filtering for only male subjects, for each type of cancer where the healthy individuals sub-group will be denoted as the control group.

In one embodiment, a user may further provide a selection of the type of statistical analysis of interest (e.g., parametric, t-test, one-way ANOVA, non-parametric, Mann-Whitney, Kruskal-Walles, etc.). This control may be provided in the Statistics Type 73 of FIG. 1B. The system can then run a statistical analysis on the sub-groups of data created in step 260 and display information pertaining to the calculations. The type of statistical values presented may include: p value of each group compared to control group, fold change in measured value between control and other biological replicate groups (e.g., by using multiple demographic information types to set up dimension of the comparison), and mean measured values of each replicate groups and statistical outputs which describe variability and inform characterization of statistically significant differences.

A summary table may be provided with statistical numbers for each sub-divided set of data, in for example a GUI display area, such as component 60 of FIG. 1B. In one embodiment, a selected control group will result in some visual mark on the display indicating which data row or data set represents the control group. Various plots generated based on the statistical analysis may be displayed for each sub-population of data. In one implementation, the control group is displayed to the very left.

The displayed graphs may be scatter plots, bar charts, box and whisker charts, or any other suitable graphical representation of statistical data. In one embodiment, a user hovering over a dot on a scatter plot will be provided a tool tip with additional information about the sample represented by the dot. The data analysis information may be displayed and/or provided to a user in any suitable form. As one example, the parameter selections may result in the creation of an export data file with statistical information based on the selections.

III. Import/Export of Data

Embodiments can also provide for data importation, modification, and enrichment. In one embodiment, a user may import data obtained from experimental runs by importing comma separated data files, or any other suitable file format that database 10 of FIG. 1A can support. In another embodiment, a user may cut-and-paste data from a spreadsheet program to be updated in the database component 10 of an automated biochemical data analysis system.

In one embodiment, database 10 can provide a base set of fields for any given dataset row. Additionally or instead of any base set of fields, a user may define new attributes for a resident dataset (e.g., either via importation or by cut-and-paste). For example, attributes may be added to provide additional characteristics applicable to the dataset, as an enrichment. Such data enrichments can be done on a project-by-project basis, allowing for custom data characterization based on the project (e.g. one study may require information about the gender and ethnicity for each experimental run, whereas such characteristics may not be relevant for another study).

Data modification can also be performed. Data resident in the system, either via importation or via cut-and-paste may be brought up in a tabular fashion for further modifications. In various embodiments, a new column can be added to the data, data can be modified by selecting a cell in the table and modifying values, data values can be selected from a cell and dragged in any direction to be copied into additional cells, and a plurality of cells may be selected and deleted to remove data values.

The biochemical analysis data can also be exported. Data exports may be advantageous particularly for importing biochemical analysis data into other statistical packages for further evaluation of the data. In one embodiment, a user may select a plurality of analytes, e.g., by highlighting one or more rows in the Analyte Data Table 50. In one aspect, upon user selection of analytes, Statistical Information Display 60 is updated with a table containing the underlying data for the selected analytes. In one embodiment, such data then may be exported for use in other systems or otherwise.

IV. User Interface

In various embodiments, data can be imported from an external database (e.g. for an existing project), files (e.g. files output by laboratory apparatus as part of an experiment) as may be done for a new project, and by hand. In one aspect, the data from the external can be from a previous session that was saved. When selecting the previous session, the data can be retrieved from the external database and input into the application, which can have an embedded database or other mechanism to organize the data. In one embodiment, in an Open (manage) projects dialog box, a user can edit project attributes, open a project, and/or remove a project from an active project list (which may cause projects to move to inactive projects that is accessible via a new tab). Thus, in one implementation, these deactivated projects may still be opened. The following screenshots provide examples according to embodiments of the present invention.

Figure 3:
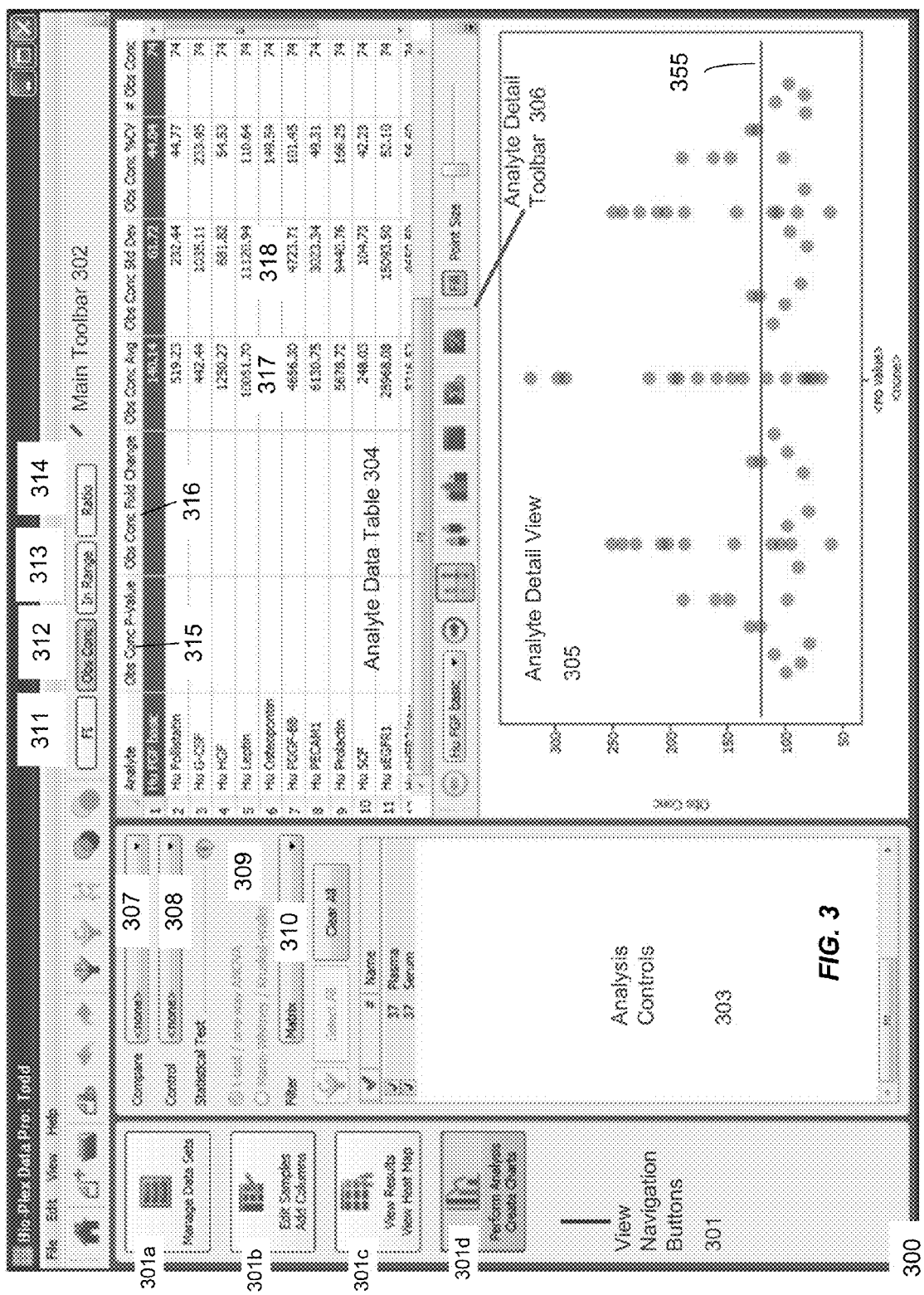
FIG. 3 shows a screenshot of a UI page of one embodiment of a biochemical analysis system, illustrating a screen where no compare field is selected, and no control group is selected.

FIG. 3 shows a screenshot of a UI page 300 of one embodiment of a biochemical analysis system. Page 300 illustrates a screen where no compare field is selected, and no control group is selected. The top right quadrant in the screen illustrates an analyte data table 304 with "Hu FGF Basic" as the selected analyte, by selection of the row for that analyte. The bottom right quadrant represents an analyte detail view 305 (e.g. a statistical display) of a scatter plot of all data samples for the selected analyte. Note that this screen shot does not provide any information by sub-populations, since no compare field has been selected by the user.

The view navigation buttons 301 can change the view presented to the user. Manage Data Sets button 301a can access a view in which the all data sets which comprise the project are listed with pertinent details. In one embodiment of this data set view, a user may perform some maintenance functions of a data set, such as edit data set attributes (e.g. name, user name, acquisition time, description, imported date, and imported by; delete the data set (permanently remove from the analysis—as opposed to filtering it); and copy the table to clipboard. The Edit Samples/Add Columns button 301b can access a view in which the customer has access to controls appropriate for annotating their data (e.g. adding sample details). A new column can be added as a custom field to the dataset. The View Results/View Heat Map button 301c can enable a view in which all experimental values (e.g., Obs Conc, In Range, etc.) are displayed in tabular form for each sample in the project. A graphical display of the heat map can also be provided. The Perform Analysis/Create Charts button 301d can allow a user to view the analysis of the samples grouped by similar attributes. The details of this view are presented elsewhere.

The main toolbar 302 provides navigation along with other functions. Buttons 311 through 314 define the data used for analysis. All are values that can be imported with the data file created by the software running the instrument. For example, the Fluorescence intensity (FI) button 311 when activated presents fluorescent values (an example of a raw instrument reading of a concentration) or calculated values derived from fluorescent values depending on the view actuated. Thus, if FI button 311 is selected, then the data shown in analyte data table 304 will reflect the fluorescent values. The Observed Concentration (Obs Conc) button 312 relates to a calculated value which is calculated based on a calibration curve generated in the instrument software. Activating this button presents Observed Concentration values or calculations derived from these values depending on the view actuated.

The In Range button 313 and the Ratio button 314 can be similarly used to change the data presented or used for calculations in each view. The In Range button 313 (i.e. Concentration in Range) relates to the concentration being within a reliable range of a calibration curve. For example, In Range button 313 can report the same values as Obs Conc, except that out of range values may be reported as OOR (Out of Range) instead of providing the actual value. The Ratio button 314 can present data of a ratio of a measurement (e.g. the FI value) normalized by a factor (e.g. normalized by another measurement of a housekeeping analyte). Any measured value can be normalized, and then statistical values can be computed from the normalized values.

The analysis controls 303 allows for various analyses of data in analysis data table 304. The compare field 307 provides a picklist (or other input mechanism) to select a parameter to be used as the compare field. The control field 308 provides a similar mechanism to select the control. The statistical options 309 provide different statistical tests for analyzing the compare field and the control. The filter option 310 provides a mechanism to select a filter parameter (e.g. from a picklist) and then enter certain filter criteria (e.g. plasma or serum) of the selected filter parameter. In some embodiments, more than one filter parameter may be selected.

In the analyte data table 304, the columns show data related to the observed concentration button 312. If another of the buttons (e.g. 311, 313, or 314) were selected, then other data can be displayed in analyte data table 304. Column 315 can show the p value from a specified test. Column 316 can show a change from sample with highest value and lowest value in selected analyte; this value can be expressed in Log base 2 or other base. In this example, no data is shown in these columns because no compare field is selected. Column 317 shows the average value of the output identified using the buttons 311-314 for all samples in the project for the each analyte. Column 318 shows the standard deviation of the output identified using the buttons 311-314 for all samples in the project for the each analyte.

In the example shown, the analyte view 305 shows the observed concentration for the selected analyte (Hu FGF basic). The data points are spread along the X axis (labeled no value) to allow better visualization to see how many data points are at a particular observed concentration. Line 355 shows the average concentration. As no compare field is chosen, the plot is for all data points for this analyte that were obtained from plasma or serum (as selected for filters). The analyte detail toolbar 306 allows the user to change the display of the analyte detail view 305.

Figure 4:
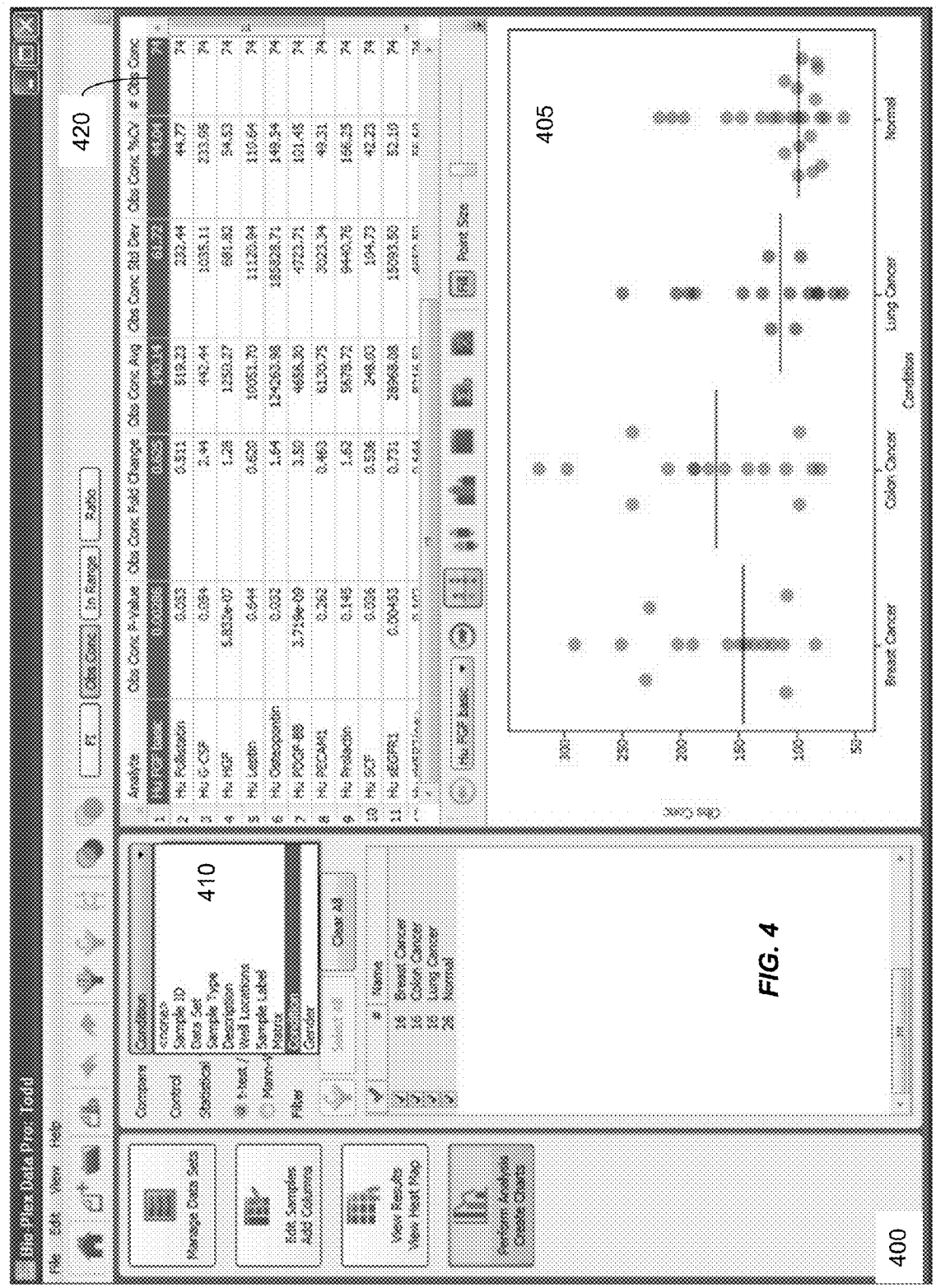
FIG. 4 is a screenshot of a UI page of one embodiment of a biochemical analysis system, illustrating a drop down list for selecting a compare field and the resulting group comparisons.

FIG. 4 is a screenshot of a UI page 400 of one embodiment of a biochemical analysis system, illustrating a drop down list for selecting a compare field. The compare field provides a drop-down list box 410, having possible values of "Sample ID", "Data Set", "Sample Type", "Description", "Well Locations", "Sample Label", "Matrix", "Condition", and "Gender". The "condition" value is shown to be selected in the compare field. The bottom right quadrant of the display shows a scatter plot, divided into data for the sub-populations of "Breast Cancer", "Colon Cancer", "Lung Cancer", and "Normal" based on the compare field selection of condition as the compare field. Thus, this embodiment has identified these four conditions in the data for the selected analyte. Also, the analyte detail toolbar between the top right quadrant and the bottom right quadrant shows various types of display and statistical information that a user can choose from for display in the bottom right quadrant. In this example, the user has selected the "scatter plot" icon as the choice of graph.

Highlighted row 420 depicts an embodiment of step 220 of method 200. It shows that the user has selected the analyte "Hu FGF Basic" for analysis. The selection shows that the dataset for the "Hu FGF Basic" analyte will be used for further analysis. Drop down list box 410 depicts one implementation of step 230. It shows that a user has selected "condition" as the field for comparison. The creation of sub-groups in step 260 may be performed in the background of the GUI application or by another separate application process. Quadrant 405 depicts an embodiment of step 270. It shows the sub-groups created for step 260, which have been statistically analyzed (e.g., in a background process), result in the four sub-groups. The resulting groups shown are "Breast Cancer", "Colon Cancer", "Lung Cancer", and "Normal". The caption below the sub-groups says "condition", denoting the user selected compare field. And the series of graphs shown are scatter plots for the four sub-populations because the user has the "scatter plot" icon as the selected type of graph of interest. In one embodiment, a user may switch between the various different information types available on the toolbar (e.g., bar graph, scatter plot, box-and-whisker graph, table of information, etc.).

Figure 5:
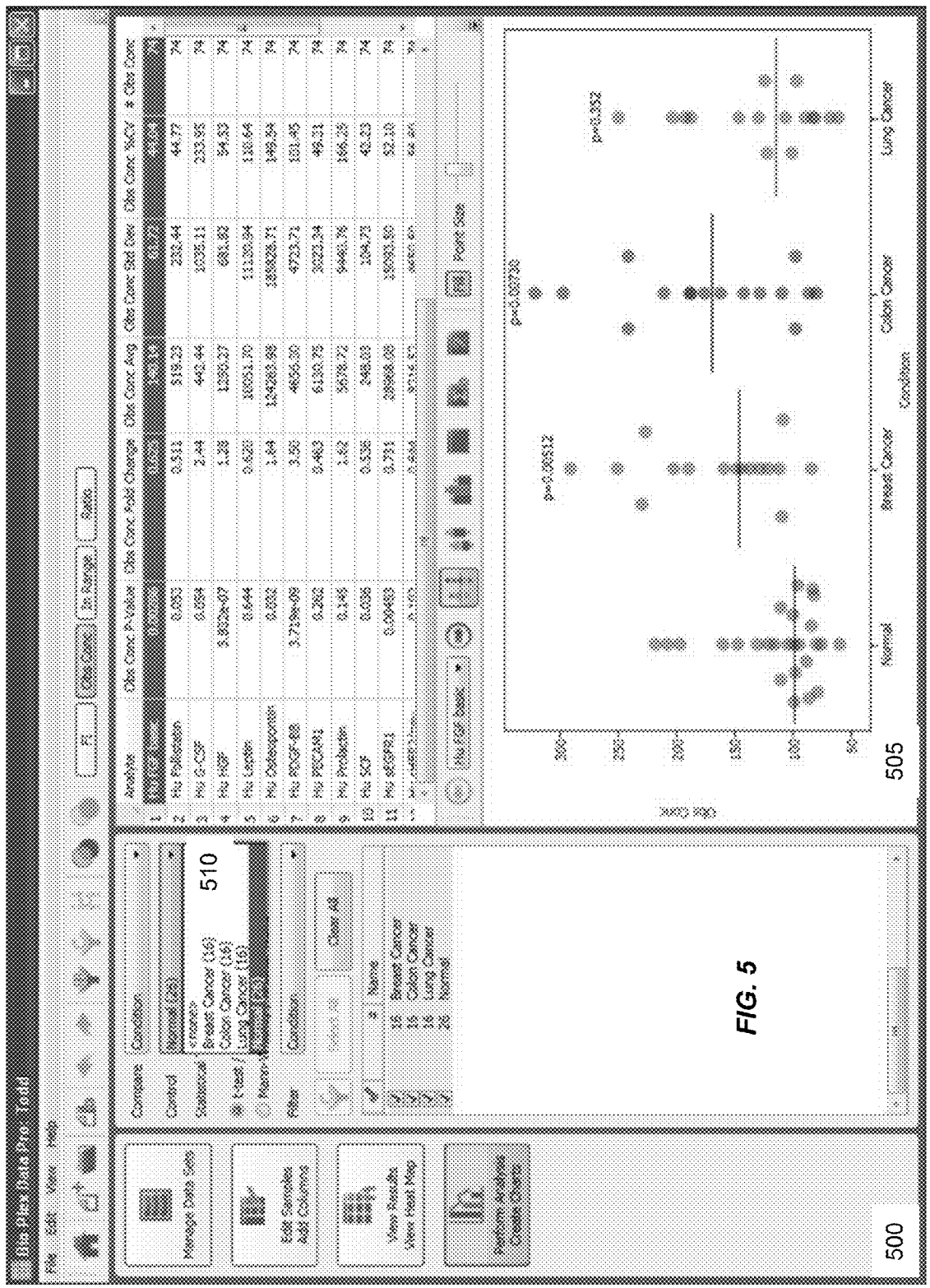
FIG. 5 is a screenshot of a UI page of one embodiment of a biochemical analysis system, illustrating a drop down list for selecting a control group and the resulting reorganization of groups and associated calculations.

FIG. 5 is a screenshot of a UI page 500 of one embodiment of a biochemical analysis system, illustrating a drop down list 510 for selecting a control group, as described in step 240 of FIG. 2. Control group selection list box 510 shows possible values of "none", "Breast Cancer", "Colon Cancer", "Lung Cancer", and "Normal". Note that the values correspond to the possible dataset values for the selected compare field of "Condition" from FIG. 4. The "Normal" value is shown to be selected as the control group.

Quadrant 505 of FIG. 5 is essentially the same as discussed for FIG. 4, with the exception that it further shows the effect of the selection of the "Normal" group as the control group. As a result of selecting "Normal" as the control group, the sub-population associated with "normal" and its scatter plot has been shifted to the very left of the scatter plots for all sub-populations. This facilitates a user to visually compare the "normal" population with other populations. FIG. 5 also shows the p-values (a statistical number) for pair-wise comparisons with the control for each sub-population in their respective scatter plots.

Figure 6:
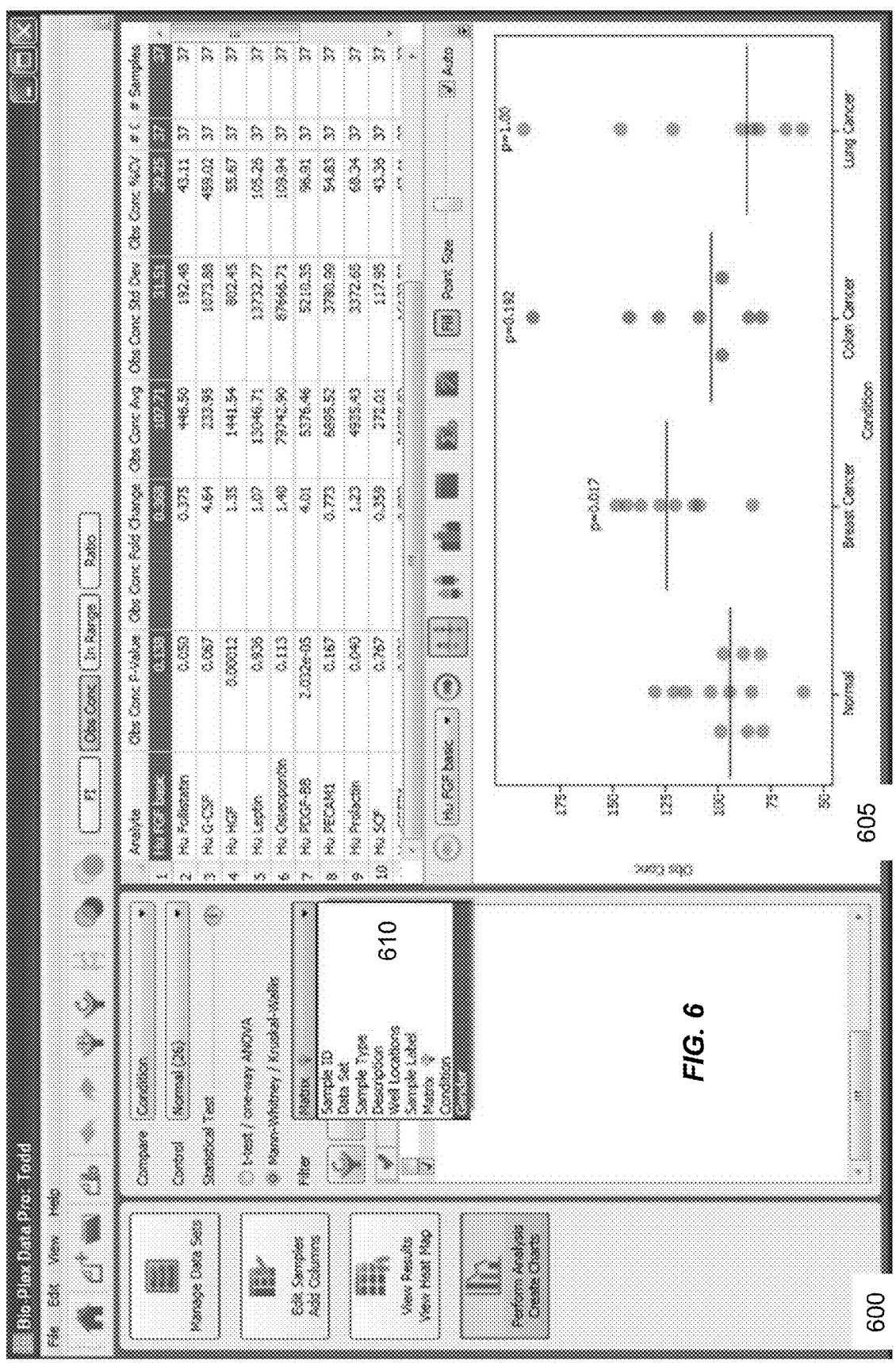
FIG. 6 is a screenshot of a UI page of one embodiment of a biochemical analysis system illustrating a drop down list for adding a filter parameter of gender and a resulting reduction in data update of calculations.

FIG. 6 is a screenshot of a UI page 600 of one embodiment of a biochemical analysis system illustrating a drop down list 610 for selecting a filter parameter, e.g., as described in step 250 of method 200. It shows a filter parameter selection list box 610 with "Gender" in the act of being selected as a filtering parameter. In this example, the possible values in the filter parameter selection box 610 are the same as those in the compare field selection list as discussed in FIG. 4. Both the compare field and filter parameter may be derived as a list of possible fields or attributes for a dataset that is being analyzed. As such, they may have the same values in the drop-down list box associated with each parameter.

Figure 7:
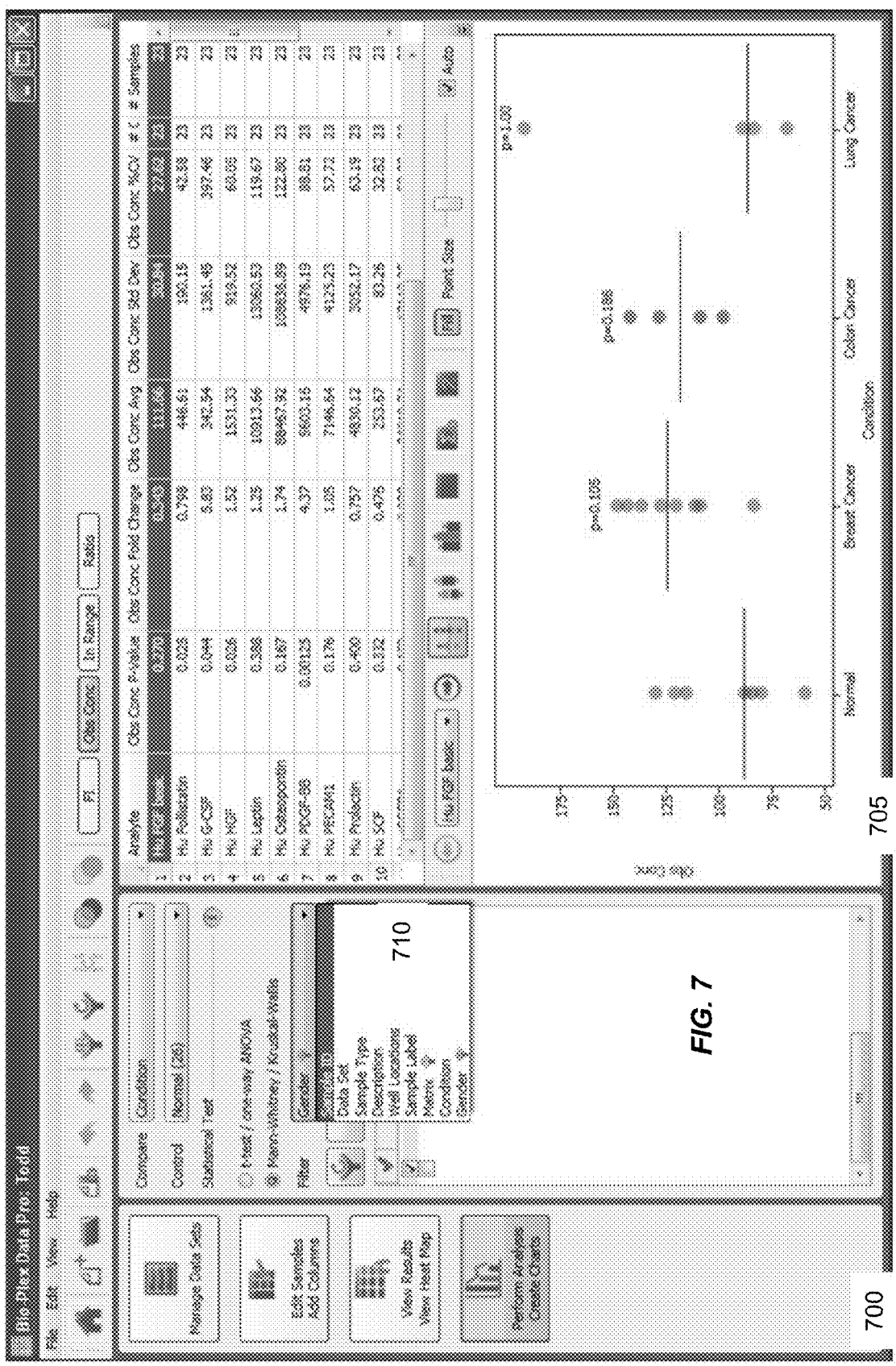
FIG. 7 is a screenshot of a UI page of one embodiment of a biochemical analysis system, illustrating a drop down list for adding a filter parameter of sample ID.

Analyte detail view 605 still shows data for only one filter parameter of matrix, as the gender criteria has not been added yet. The filter criteria of serum is only checked, and plasma is unchecked as a filter criteria. In this implementation, matrix refers to the fluid or substance in which a reaction is taking place, which can describe the type of sample (e.g., serum, plasma, cell culture supernatent). Since a gender filter has not been implemented yet, the analyte detail view shows results of the application of both gender (Female only) and Matrix (serum) in the scatterplot FIG. 7 is a screenshot of a UI page 700 of one embodiment of a biochemical analysis system illustrating a drop down list 710 for adding a filter parameter of sample ID. Here, it shows a filter parameter selection list box 710 with both "Gender" and "Matrix" selected as the filtering parameter, with the parameter in the process of being changed to Sample ID. Filter parameters that are being used are marked, as can be seen in FIG. 7. Analyte detail view 705 shows data for the filters of both gender (Female only) and Matrix (serum) in the scatterplot.

Figure 8:
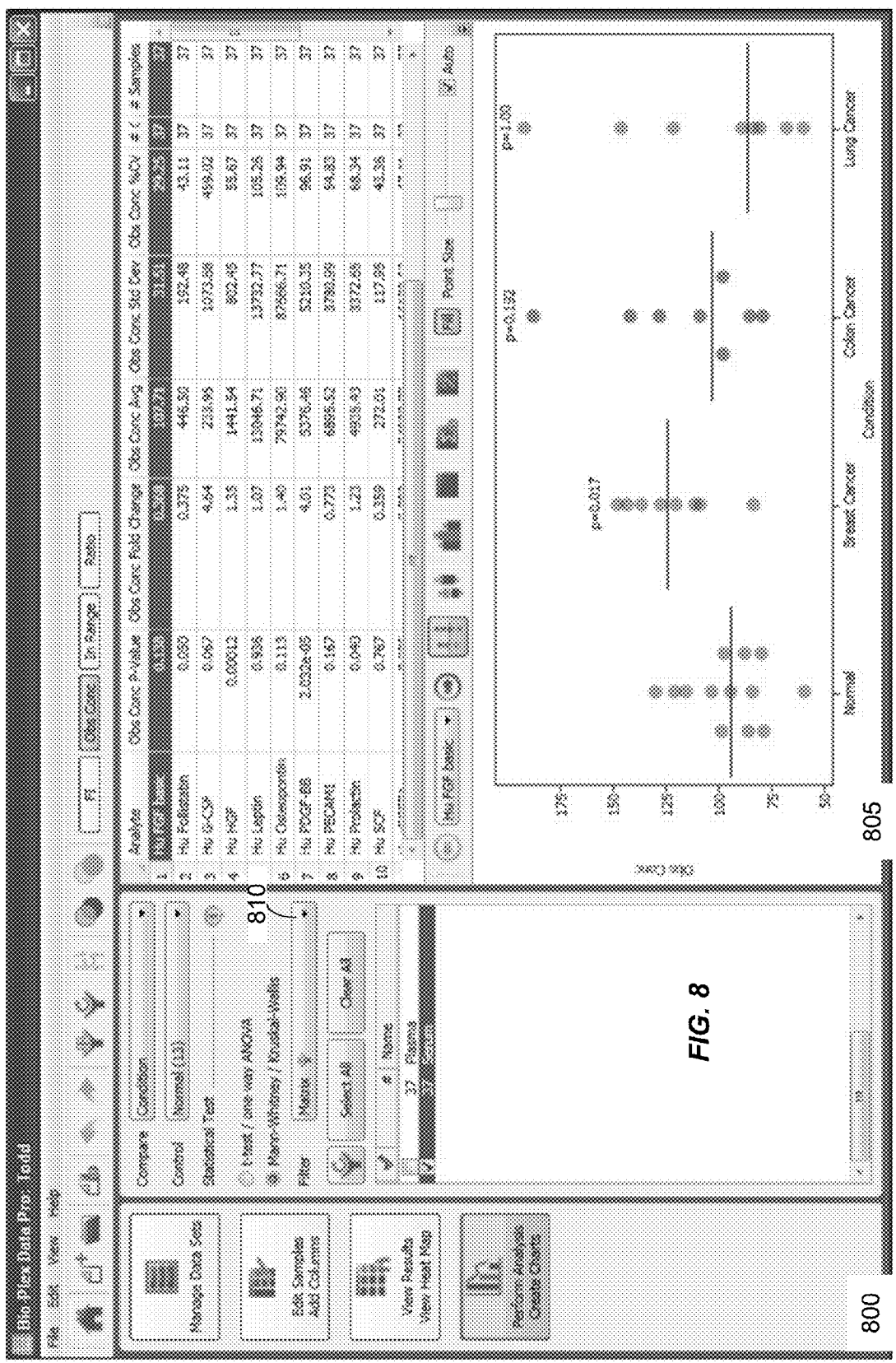
FIG. 8 is a screenshot of a UI page of one embodiment of a biochemical analysis system, illustrating checkboxes for selecting filtering criteria.

FIG. 8 is a screenshot of a UI page 800 of one embodiment of a biochemical analysis system, illustrating checkboxes for selecting filtering criteria, e.g., as in step 250 of method 200. It shows that the possible filtering criteria checkboxes are "plasma" and/or "serum". Note this is based on the user's selection of "Matrix" as the filtering parameter. It further shows that only "serum" samples are selected for dataset analysis. In one implementation, the filter shown in the picklist 810 controls what filter criteria are displayed. To determine all of the filter criteria being used, one can identify the parameter being used (e.g. as those marked by the filter icon when the picklist 810 is enabled) and then navigate to each to see which criteria are selected. The criteria shown for a particular parameter can be set by default or depend on which values actually occur in the dataset.

An impact of the selection of the filtering criteria is to select only those dataset rows that have the checked values for the filter parameter selected, e.g., as at step 250. Quadrant 805 shows the effect of filtering the dataset for only samples with "serum" as the data value for the "Matrix" attribute in the dataset. It shows a corresponding decrease in the number of dots on the scatter plot as compared to FIG. 5 where no further filtering criteria were selected by the user. A user could instead select "plasma" as the samples of interest. In one aspect, a user could check both "Plasma" and "Serum", however the net effect of a user selecting all possible values would be no filtering since all samples would then be selected.

Figure 9:
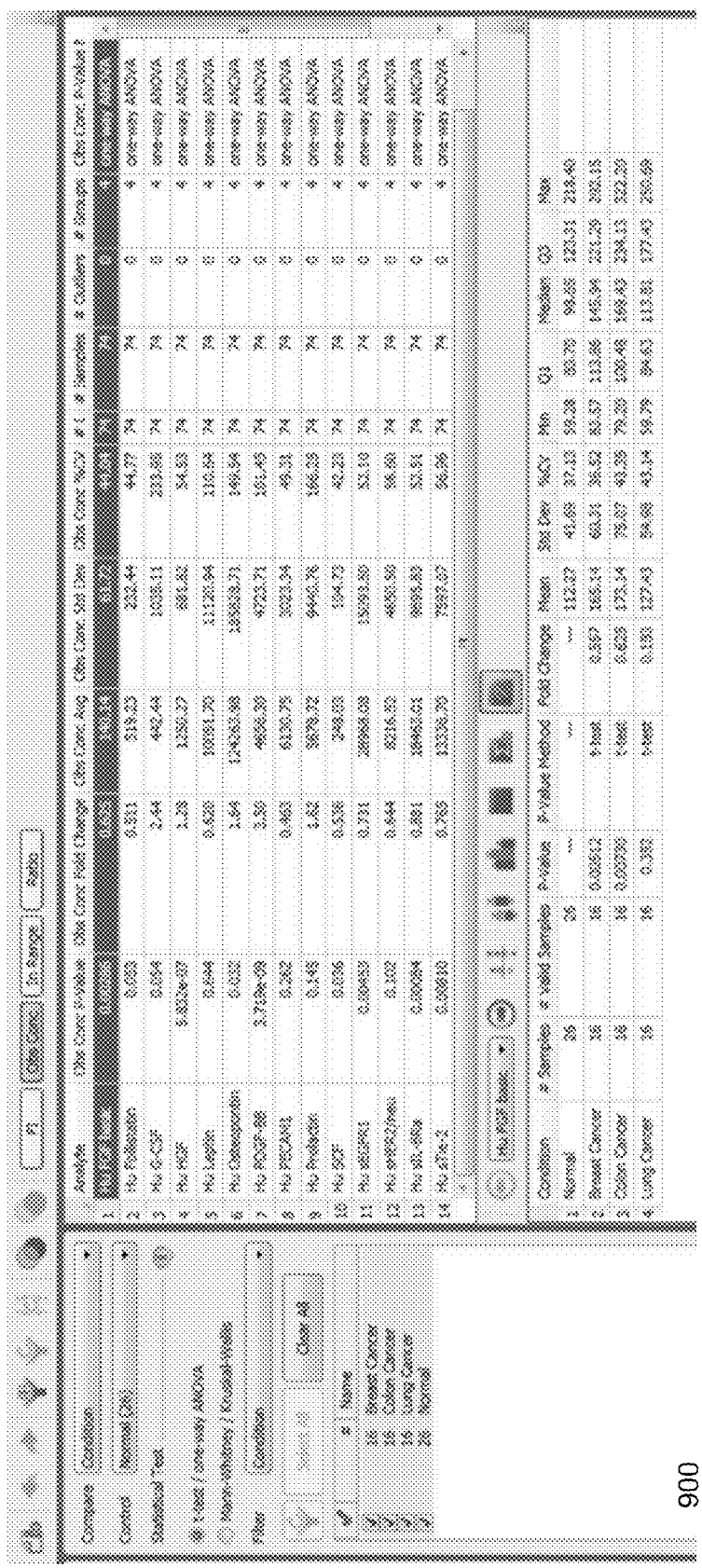
FIG. 9 is a screenshot of a UI page of one embodiment of a biochemical analysis system showing statistical summaries, illustrating a view where the compare field is selected as "condition", the control group is selected as "normal", the filter condition is set to "condition", and all conditions are selected as filtering criteria.

FIG. 9 is a screenshot of a UI page 900 of one embodiment of a biochemical analysis system showing statistical summaries, illustrating a view where the compare field is selected as "condition", the control group is selected as "normal", and no further filtering of the data is provided (i.e. because all condition criteria are selected for the condition filter parameter and no other filters are applied). Quadrant 905 of the display shows a table with statistical numbers for each sub-population based on the selection of "condition" as the compare field. It further shows the "Normal" sub-population on the very top based on the user selection of "Normal" as the control group. This summary table shows explicitly the calculations that result from the choices made in the compare and control pull downs.

As shown, the calculations are of the value specified in the main toolbar. In this example, the selected value is the observed concentration 912. The values in the columns are as follows: Samples—number total samples in each group; # valid samples—number of samples with data which is valid for performing calculations; P-value—for the test specified in p—value method; Fold change—between mean of the control and mean of each group expressed in log base 2 (which is different from the fold change in the analyte table); Mean—arithmetic mean of all samples in group; Std Dev—is the standard deviation for all valid samples in group; % CV—is the coefficient of variation for all valid samples in group; Min and Max are the minimum and maximum value for the group; Q1 and Q3 are the first and third quartile for the group; and Median is the median value for the group.

Figure 10:
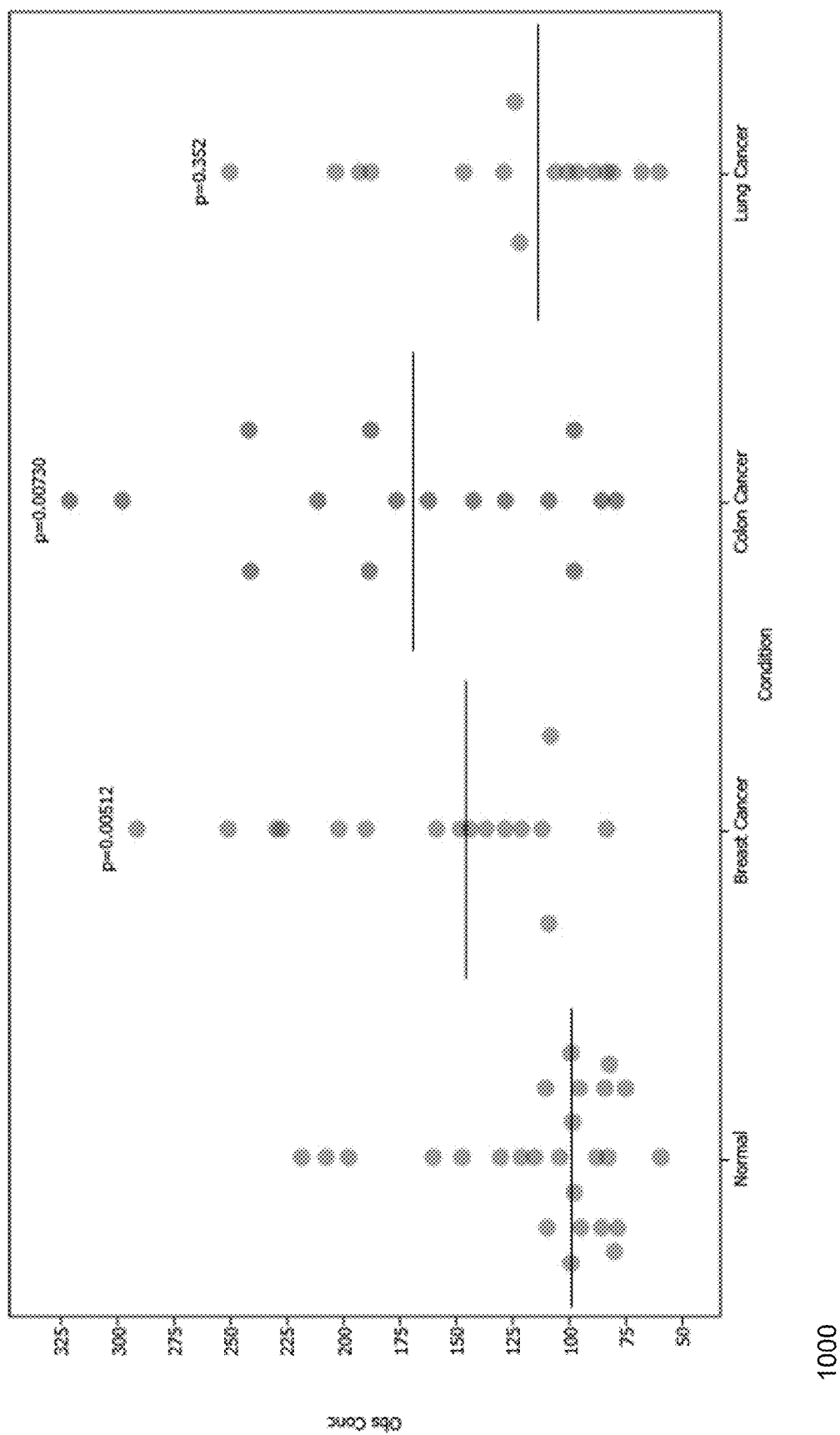
FIG. 10 is scatter plot 1000 of a UI page according to embodiments of the present invention.

FIG. 10 is scatter plot 1000 of a UI page according to embodiments of the present invention. The scatter plot here is a blown up view a quadrant that may be displayed in UI pages shown herein. In one embodiment, the dots are spread on the x axis so that a 'mouse over' results in pertinent sample information being presented to the user. In combination or separately, other embodiments can have the ability to mark a particular sample to track through other analytes, mark a particular attribute of a sample in order to track it through the other groups (e.g. to graphically call out a particular patient in order to visualize through this plot), and double click on a dot in order to recall a table with all demographic information. In other embodiments, other plots may be displayed, such as a "box and whisker" type of chart and a "bar graph" type of chart.

Figure 11:
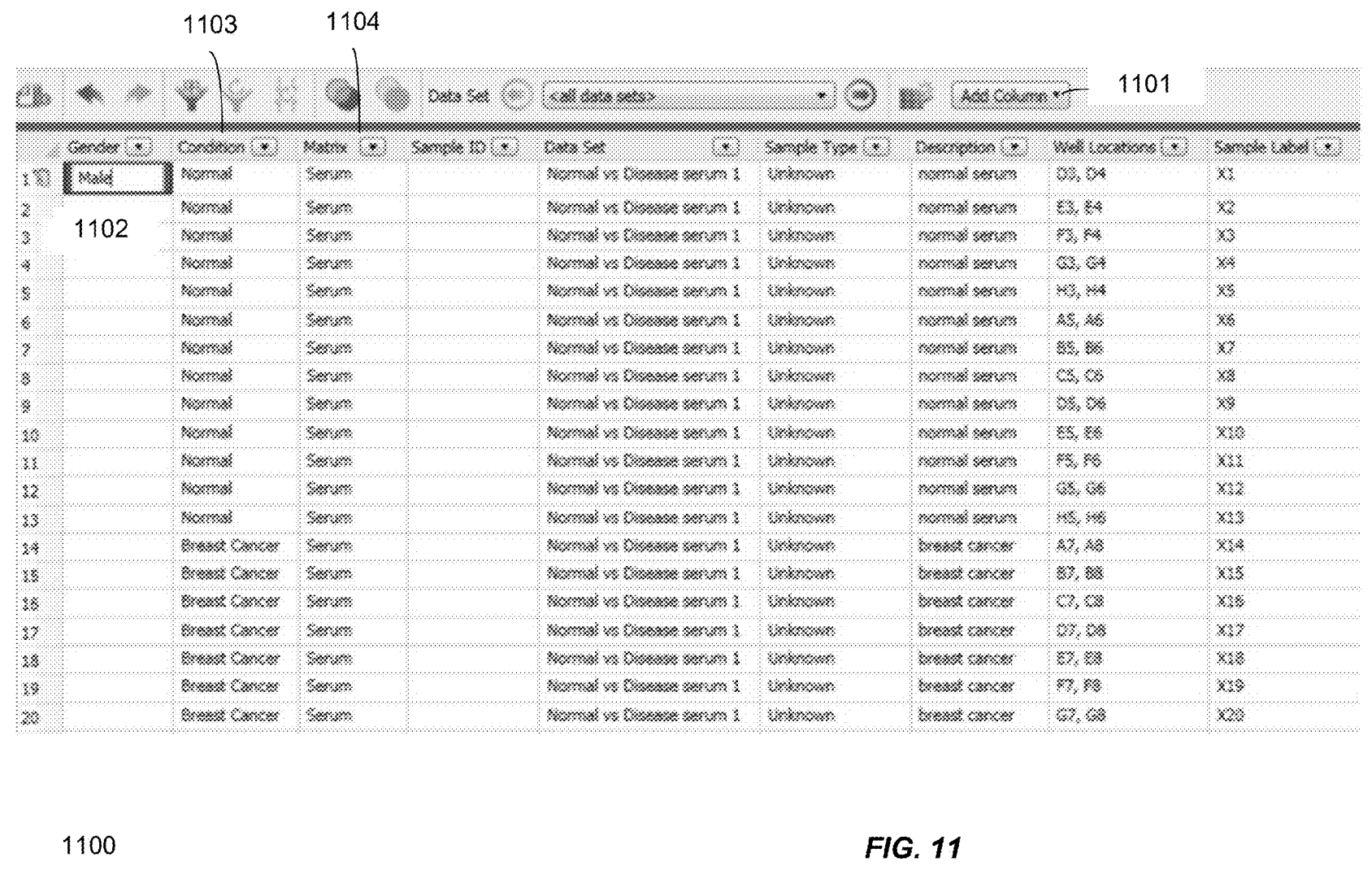

FIG. 11 is a screenshot of a UI page 1100 of one embodiment of a biochemical analysis system, illustrating one example of data modification of the system. As example, the data presented in a tabular fashion may have been either imported into the system or cut-and-pasted from an excel sheet. The display shows how a "gender" column either newly added as a custom field or pre-existing can be further modified by the user by entering data for the column such as the value of "male" for the first cell.

In this example, this display can be accessed by selecting the edit samples/edit columns button 301b of the view navigation buttons 301 in UI page 300. In one aspect, this display can show every sample (without repeats) in all the data sets imported into a project. In one embodiment, an Add column button 1101 allows the addition of a custom column (attribute) to the list of samples. The number of columns that can be added may be configured to be unlimited or to be capped. The column 1102 demonstrates a newly added column in which information is being added. In one embodiment, the columns Condition 1103 and Matrix 1104 may not be present in the originally data imported from a laboratory apparatus that performs a measurement, but is tracked in another manner. For instance, the Condition and Matrix may be added by a technician who is running the sample and knows the condition and matrix through other channels (e.g. a questionnaire taken of a patient or marked by a medical professional who took the sample).

In one embodiment to export data, a user can select multiple analytes. The data for exporting can show up in the analyte detail view 305 of page 300. Analyte detail view 305 can show the underlying dataset for the selected analytes. Such data can then be exported for use in other systems or for any other purpose. In one aspect, choosing a compare field and applying filters make the application particularly well suited for creating these tables. Raw data or data resulting from a calculation can be exported.

V. Example Workflows

There are many possible sequences of events which a user might use when analyzing their data. In one example, a user can import two data files (e.g. as part of a new project) and then add information in new columns, as described in FIG. 11. The user can then choose the compare field "Condition" as seen in FIG. 4, and choose the control 'Normal' as seen in FIG. 5. The user might then decide that the data might be more interpretable if only samples derived from serum are used, as in FIG. 8. The display in the analyte detail view can be updated based on these selections. The user might also want to investigate whether females are demonstrating different analyte levels compared to males, e.g. by first using a filter for female to display female only data, and then using the filter to display male only data. In one embodiment, when application closes the project, the last compare, control and filter selection can persist in the project.

In another example, a user can import different instrument results files, and then add information, as in progress in FIG. 11. The user can decide there is an issue with readings from Well number A1 and exclude this well from the analysis by using the filter tool with parameter "well location", thereby eliminating it from all data files in one mouse click. As in the other example, the user could choose to only analyze samples from 'Serum.' Selections for the compare field "Condition' and control field 'normal' can be made. The user can then review results for each analyte separately and draws conclusions. Now, if the user returns to the data two weeks later after he has identified an instrument run in which the instrument was not performing properly, the user can delete data file #13 (e.g. using the manage data sets view) from the analysis and reviews data again by analyte to draw conclusions. The user can also rerun the samples from data file #13 and imports the data file to the project, add sample information for the new samples, and review results by analyte to draw conclusions.

In another example, the user may want to save one or more "analysis methods." As above, the user imports 15 different instrument results files, adds information, eliminates a well, selects on 'Serum', chooses the compare field "Condition' and control field 'normal', and then reviews results for each analyte separately and draws conclusions. The user can save this analysis state as "Serum only." The user can then change the filter to "Plasma" and save this analysis state "Plasma only." The user can remove the males from an analysis and saves this as "Plasma only, Females." In one implementation, the user can return at a later date and retrieve each Compare selection, Control Selection and filter state as needed to draws conclusions about the experimental system.

VI. Flow Cytometry

In one embodiment, flow cytometry can be used to measure a concentration. Thus, the experiments described above for measuring a concentration can involve flow cytometry. The analyte whose concentration is measured can be, for example, a cell type or a particular molecule. In one implementation, flow cytometry can be used to count a number of cells of a particular type (e.g., red or white blood cells, and other cell types of interest, as well as pathogens like bacteria and viruses). This count can be used directly as a concentration, or normalized based on an amount of the sample (e.g., weight or volume) or count of another cell type. Flow cytometry can allow a user to characterize cell populations very rapidly. In another implementation, a signal intensity (e.g., fluorescence) can be used to detect particular molecules, such as glucose.

Flow cytometry passes cells from a sample single file past a detection mechanisms that makes use of light emitters (usually lasers) and detectors placed both directly across from and perpendicular to the incident light. Generally there are two types of parameters that can be used independently or together to characterize a population: physical cell characteristics and fluorescence intensity of a specific fluorescent label. Thus, the data to be processed and displayed can include counts and fluorescence. For the counts, researchers can track the number of cells in each cell type (e.g., gated population) per a sample. For fluorescence, researchers can track the fluorescence levels at many wavelengths to identify the presence and quantity of specific biomolecules.

To determine physical cell characteristics, the analysis can make use of side scatter and fluorescence scatter data to characterize cells. There is a size correlation to fluorescence scatter (the more scatter, the larger volume of the cell that the light is interacting with), and side scatter can be used to further characterized the cells. Different amount of side scatter can indicate different levels of complexity, organelle density and size etc. The two scatter read outs can be used to create a profile for the different populations of cells in the sample. If a scatter read out matches a profile then a counter for the corresponding population can be incremented. Thus, one can count the number of cells which belong to the different populations within the sample of interest.

Accordingly, for cell characteristics, the instrument and software, which processes the data, can allow the researcher to use the scatter information to identify cell populations. The data may be plotted on a graph, which indicates the level of fluorescence scatter vs. side scatter for each cell that passes the detector. The user can define populations by essentially drawing circles around the discrete populations, which is called gating. Each circle can be considered a gate. The same gate is used for every sample, and all the cells that fall within a given gate are considered part of a population of interest.

Fluorescence intensity of a specific fluorescent label can be used to label a naturally occurring molecule on a cell for evaluation of presence and density of the molecule on the cell (other technologies besides a fluorescent label can also be used). Typically, an antibody is used to specifically identify the presence and quantity of a specific biomolecule of interest on (or less commonly within) a cell. This antibody can be labeled in a variety of ways to produce a fluorescence in a defined wavelength which can be detected by the instrument and its associated software. Most instruments can detect three or more different wavelengths for the purpose of detecting multiple biomolecules of interest. If a cell has a biomolecule of interest on it, fluorescence will be detected at a specific wavelength. The intensity of that fluorescence is directly proportional to the amount of the biomolecule present.

As an example, the researcher may be interested in the following: four different cell types that fall into four specific gates, and three biomolecules which are present in the membranes of the cells at concentrations which vary in their experimental system. So for each sample, one would want a count for each of the gates 1 through 4 as well as an average (or mean, or median or mode) of fluorescence intensity for each of the three fluorescent markers in each population. For instance one could obtain the data in the following table.

| Sample | Gate | Count | Flourescence1 | Flourescence2 | Flourescence3 |
|--------|------|-------|---------------|---------------|---------------|
| 1 | 1 | $1.2 \times 10^6$ | 2344 | 98 | 2090 |

The actual scatter data and their associated graphs for each sample can be stored in the database. One can then look at a list of the gates and click through to an image of the light scatter plot from which the gated data was extracted.

VII. Computer System

Figure 12:
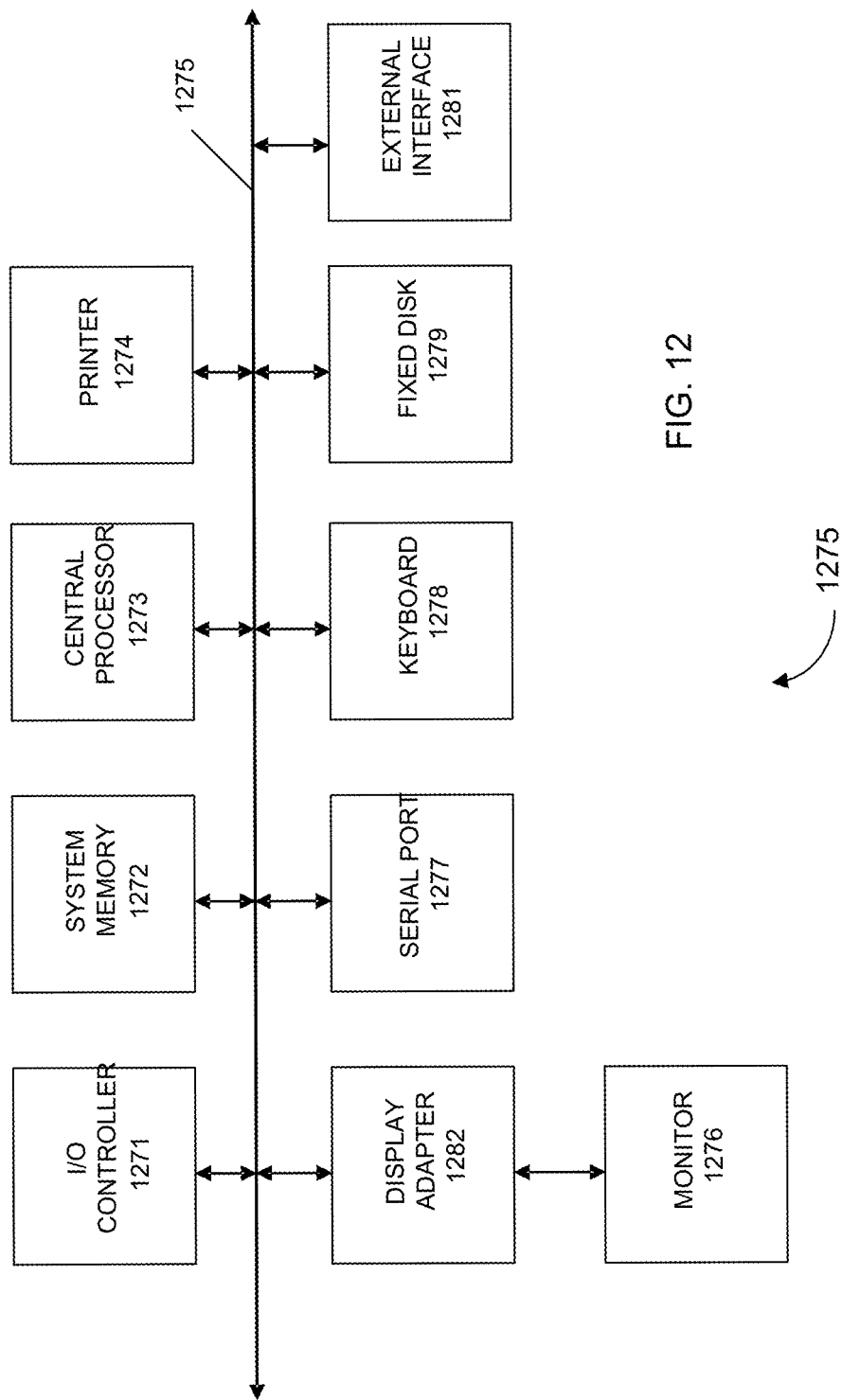
FIG. 12 shows a block diagram of an example computer system 1200 usable with system and methods according to embodiments of the present invention.

Any of the computer systems mentioned herein may utilize any suitable number of subsystems. Examples of such subsystems are shown in FIG. 12 in computer apparatus 1200. In some embodiments, a computer system includes a single computer apparatus, where the subsystems can be the components of the computer apparatus. In other embodiments, a computer system can include multiple computer apparatuses, each being a subsystem, with internal components.

The subsystems shown in FIG. 12 are interconnected via a system bus 1275. Additional subsystems such as a printer 1274, keyboard 1278, fixed disk 1279, monitor 1276, which is coupled to display adapter 1282, and others are shown. Peripherals and input/output (I/O) devices, which couple to I/O controller 1271, can be connected to the computer system by any number of means known in the art, such as serial port 1277 (e.g. USB). For example, serial port 1277 or external interface 1281 can be used to connect computer system 1200 to a wide area network such as the Internet, a mouse input device, or a scanner. The interconnection via system bus 1275 allows the central processor 1273 to communicate with each subsystem and to control the execution of instructions from system memory 1272 or the fixed disk 1279, as well as the exchange of information between subsystems. The system memory 1272 and/or the fixed disk 1279 may embody a computer readable medium. Any of the values mentioned herein can be output from one component to another component and can be output to the user.

A computer system can include a plurality of the same components or subsystems, e.g., connected together by external interface 1281 or by an internal interface. In some embodiments, computer systems, subsystem, or apparatuses can communicate over a network. In such instances, one computer can be considered a client and another computer a server, where each can be part of a same computer system. A client and a server can each include multiple systems, subsystems, or components.

It should be understood that any of the embodiments of the present invention can be implemented in the form of control logic using hardware and/or using computer software in a modular or integrated manner. Based on the disclosure and teachings provided herein, a person of ordinary skill in the art will know and appreciate other ways and/or methods to implement embodiments of the present invention using hardware and a combination of hardware and software.

Any of the software components or functions described in this application may be implemented as software code to be executed by a processor using any suitable computer language such as, for example, Java, C++ or Perl using, for example, conventional or object-oriented techniques. The software code may be stored as a series of instructions or commands on a computer readable medium for storage and/or transmission, suitable media include random access memory (RAM), a read only memory (ROM), a magnetic medium such as a hard-drive or a floppy disk, or an optical medium such as a compact disk (CD) or DVD (digital versatile disk), flash memory, and the like. The computer readable medium may be any combination of such storage or transmission devices.

Such programs may also be encoded and transmitted using carrier signals adapted for transmission via wired, optical, and/or wireless networks conforming to a variety of protocols, including the Internet. As such, a computer readable medium according to an embodiment of the present invention may be created using a data signal encoded with such programs. Computer readable media encoded with the program code may be packaged with a compatible device or provided separately from other devices (e.g., via Internet download). Any such computer readable medium may reside on or within a single computer program product (e.g. a hard drive, a CD, or an entire computer system), and may be present on or within different computer program products within a system or network. A computer system may include a monitor, printer, or other suitable display for providing any of the results mentioned herein to a user.

Any of the methods described herein may be totally or partially performed with a computer system including a processor, which can be configured to perform the steps. Thus, embodiments can be directed to computer systems configured to perform the steps of any of the methods described herein, potentially with different components performing a respective steps or a respective group of steps. Although presented as numbered steps, steps of methods herein can be performed at a same time or in a different order. Additionally, portions of these steps may be used with portions of other steps from other methods. Also, all or portions of a step may be optional. Additionally, any of the steps of any of the methods can be performed with modules, circuits, or other means for performing these steps.

Any of the above embodiments may be used alone or together with one another in any combination. Inventions encompassed within this specification may also include embodiments that are only partially mentioned or alluded to or are not mentioned or alluded to at all in this brief summary or in the abstract. Although various embodiments of the invention may have been motivated by various deficiencies with the prior art, which may be discussed or alluded to in one or more places in the specification, the embodiments of the invention do not necessarily address any of these deficiencies. In other words, different embodiments of the invention may address different deficiencies that may be discussed in the specification. Some embodiments may only partially address some deficiencies or just one deficiency that may be discussed in the specification, and some embodiments may not address any of these deficiencies.

The above description of exemplary embodiments of the invention has been presented for the purposes of illustration and description. It is not intended to be exhaustive or to limit the invention to the precise form described, and many modifications and variations are possible in light of the teaching above. The embodiments were chosen and described in order to best explain the principles of the invention and its practical applications to thereby enable others skilled in the art to best utilize the invention in various embodiments and with various modifications as are suited to the particular use contemplated.

A recitation of "a", "an" or "the" is intended to mean "one or more" unless specifically indicated to the contrary.

All patents, patent applications, publications, and descriptions mentioned above are herein incorporated by reference in their entirety for all purposes. None is admitted to be prior art.

What is claimed is:

1. A method of biochemical data analysis, the method comprising:

receiving, at a computer system, a dataset for a plurality of biological samples, the dataset having a plurality of fields for each biological sample, at least a portion of the dataset being obtained from experiments involving the biological samples, wherein the dataset includes:
a plurality of first fields, each first field including a plurality of values, each value corresponding to a respective characteristic of a respective biological sample, and
a plurality of second fields, each second field corresponding to a respective analyte and including a plurality of concentrations of the respective analyte in the experiments, each concentration corresponding to a respective biological sample;

in response to a user selecting the dataset via a graphical user interface (GUI) page of the computer system, automatically populating a drop-down box of the GUI page with the plurality of first fields, wherein the user uses an input device to select the dataset in the GUI page;

displaying, on a display of the computer system, a list of the plurality of first fields in a first region of the GUI page in response to the user selecting the drop-down box in the GUI page, wherein the user uses the input device to select the drop-down box;

receiving, at the GUI page, a selection of a compare field from the list of the plurality of first fields, wherein the user uses the input device to select the compare field;

in response to the user selecting the compare field, automatically identifying a plurality of values in the database for the selected compare field;

identifying, by the computer system, subgroups of the biological samples in the dataset for statistical analysis based on the identified plurality of values for the selected compare field, wherein biological samples of a subgroup have a same value for the compare field;

in further response to the user selecting the dataset, automatically displaying, on the display of the computer system, a list of the plurality of second fields in a second region of the GUI page;

receiving, at the GUI page, a selection of an analyte from the list of the plurality of second fields displayed on the display of the computer system for statistical analysis, wherein the user uses the input device to select the analyte;

in response to the user selecting the analyte, retrieving a plurality of concentrations of the selected analyte from the dataset;

in response to the user selecting the analyte and the compare field, automatically displaying, on the display of the computer system, information of the retrieved plurality of concentrations separated by subgroups to convey statistical information for the selected analyte for each subgroup of the compare field, wherein the information of the retrieved plurality of concentrations separated by subgroups is displayed within a third region of the GUI page to facilitate visual comparison;

receiving, at the GUI page, a selection of a control group from a control group list, wherein the user uses the input device to select the control group; and in response to the user selecting the control group, automatically displaying, on the display of the computer system, a visual indication as to which subgroup corresponds to the control group.

2. The method of claim 1, further comprising:
in response to the user selecting the compare field, automatically updating the control group list based on the selection of the compare field, wherein the control group represents a particular data value from the plurality of values of the compare field.

3. The method of claim 1, wherein the display of statistical information includes a series of graphs, each graph corresponding to a different subgroup, and wherein the visual indication includes displaying the graph corresponding to the control group in a left justified manner.

4. The method of claim 1, further comprising:
receiving a selection of a first filter parameter from a filter parameter list, wherein the filter parameter list includes at least a portion of the plurality of first fields, the first filter parameter having a plurality of first criteria values;
receiving a selection of a portion of the plurality of first criteria values; and
displaying statistical information corresponding to the selected portion and not to the non-selected first criteria values.

5. The method of claim 1, wherein providing a display of information separated by subgroups includes:
displaying a graph for each subgroup, wherein each graph displays each concentration of the subgroup along an axis of concentration value.

6. The method of claim 1, further comprising:
receiving, at the GUI page, a selection of a second analyte from the list of the plurality of second fields for statistical analysis, wherein the user uses the input device to select the second analyte;
in response to the user selecting the second analyte, retrieving a plurality of second concentrations of the selected second analyte from the dataset; and
in response to the user selecting the second analyte, automatically updating the display of the computer system to display information of the retrieved plurality of second concentrations separated by subgroups to convey statistical information for the selected second analyte for each subgroup of the compare field.

7. The method of claim 1, wherein the input device is a mouse.

8. The method of claim 1, wherein the display of the computer system is a monitor.

9. The method of claim 2, wherein the control group list includes all unique possible data values for the selected compare field.

10. A method of biochemical data analysis, the method comprising:
receiving, at a computer system, a dataset for a plurality of biological samples, the dataset having a plurality of fields for each biological sample, at least a portion of the dataset being obtained from experiments involving the biological samples, wherein the dataset includes:
a plurality of first fields, each first field including a plurality of values, each value corresponding to a respective characteristic of a respective biological sample, and
a plurality of second fields, each second field corresponding to a respective analyte and including a plurality of concentrations of the respective analyte in the experiments, each concentration corresponding to a respective biological sample;

in response to a user selecting the dataset via a graphical user interface (GUI) page of the computer system, automatically populating a drop-down box of the GUI page with the plurality of first fields, wherein the user uses an input device to select the dataset in the GUI page;

displaying, on a display of the computer system, a list of the plurality of first fields in a first region of the GUI page in response to the user selecting the drop-down box in the GUI page, wherein the user uses the input device to select the drop-down box;

receiving, at the GUI page, a selection of a compare field from the list of the plurality of first fields, wherein the user uses the input device to select the compare field;

in response to the user selecting the compare field, automatically identifying a plurality of values in the database for the selected compare field;

identifying, by the computer system, subgroups of the biological samples in the dataset for statistical analysis based on the identified plurality of values for the selected compare field, wherein biological samples of a subgroup have a same value for the compare field;

in further response to the user selecting the dataset, automatically displaying, on the display of the computer system, a list of the plurality of second fields in a second region of the GUI page;

receiving, at the GUI page, a selection of an analyte from the list of the plurality of second fields displayed on the display of the computer system for statistical analysis, wherein the user uses the input device to select the analyte;

in response to the user selecting the analyte, retrieving a plurality of concentrations of the selected analyte from the dataset;

in response to the user selecting the analyte and the compare field, automatically displaying, on the display of the computer system, information of the retrieved plurality of concentrations separated by subgroups to convey statistical information for the selected analyte for each subgroup of the compare field, wherein the information of the retrieved plurality of concentrations separated by subgroups is displayed within a third region of the GUI page to facilitate visual comparison;

receiving, at the GUI page, a selection of a first filter parameter from a filter parameter list, wherein the filter parameter list includes at least a portion of the plurality of first fields, the first filter parameter having a plurality of first criteria values;

receiving, at the GUI page, a selection of a portion of the plurality of first criteria values;

in response to the user selecting the portion, automatically displaying, on the display of the computer system, statistical information corresponding to the selected portion and not to the non-selected first criteria values;

refreshing a user view of possible criteria values based on the selected first filter parameter, wherein the possible criteria values allow filtering of data on which a statistical analysis is performed;

receiving, at the GUI page, one or more user selections of criteria values based on the refreshed user view; and in response to the user selecting the criteria values, automatically filtering the subgroups of data for statistical analysis based on the selected filtering criteria.

11. The method of claim 10, further comprising:
receiving a selection of a second filter parameter from the filter parameter list, the second filter parameter having a plurality of second criteria values;
receiving a selection of a portion of the plurality of second criteria values; and
displaying statistical information corresponding to the selected portion of the first and second criteria values and not to the non-selected first and second criteria values.

12. The method of claim 10, wherein the first filter parameter is not the compare field.

13. The method of claim 10, further comprising:
receiving a selection of a type of statistical analysis;
calculating one or more statistical values for the data corresponding to the selected analyte based on the received type of statistical analysis; and
displaying the one or more statistical values.

14. A method of biochemical data analysis, the method comprising:
receiving, at a computer system, a dataset for a plurality of biological samples, the dataset having a plurality of fields for each biological sample, at least a portion of the dataset being obtained from experiments involving the biological samples, wherein the dataset includes:
a plurality of first fields, each first field including a plurality of values, each value corresponding to a respective characteristic of a respective biological sample, and
a plurality of second fields, each second field corresponding to a respective analyte and including a plurality of concentrations of the respective analyte in the experiments, each concentration corresponding to a respective biological sample;

in response to a user selecting the dataset via a graphical user interface (GUI) page of the computer system, automatically populating a drop-down box of the GUI page with the plurality of first fields, wherein the user uses an input device to select the dataset in the GUI page;

displaying, on a display of the computer system, a list of the plurality of first fields in a first region of the GUI page in response to the user selecting the drop-down box in the GUI page, wherein the user uses the input device to select the drop-down box;

receiving, at the GUI page, a selection of a compare field from the list of the plurality of first fields, wherein the user uses the input device to select the compare field;

in response to the user selecting the compare field, automatically identifying a plurality of values in the database for the selected compare field;

identifying, by the computer system, subgroups of the biological samples in the dataset for statistical analysis based on the identified plurality of values for the selected compare field, wherein biological samples of a subgroup have a same value for the compare field;

in further response to the user selecting the dataset, automatically displaying, on the display of the computer system, a list of the plurality of second fields in a second region of the GUI page;

receiving, at the GUI page, a selection of an analyte from the list of the plurality of second fields displayed on the display of the computer system for statistical analysis, wherein the user uses the input device to select the analyte;

in response to the user selecting the analyte, retrieving a plurality of concentrations of the selected analyte from the dataset;

in response to the user selecting the analyte and the compare field, automatically displaying, on the display of the computer system, information of the retrieved plurality of concentrations separated by subgroups to convey statistical information for the selected analyte for each subgroup of the compare field, wherein the information of the retrieved plurality of concentrations separated by subgroups is displayed within a third region of the GUI page to facilitate visual comparison;

receiving, at the GUI page, a selection of a type of statistical analysis;

in response to the user selecting the type of statistical analysis, automatically calculating one or more statistical values for the data corresponding to the selected analyte based on the received type of statistical analysis; and displaying, on the display of the computer system, the one or more statistical values in the table in one or more cells corresponding to the selected analyte.

15. The method of claim 14, further comprising:
receiving a definition of a custom attribute for the dataset for the plurality of biological samples, wherein the custom attribute is a user-supplied attribute that corresponds to one of the plurality of first fields.

16. The method of claim 14, wherein at least one of the plurality of second fields corresponds to a cell type as the respective analyte.

17. A computer program product comprising a tangible non-transitory computer readable medium storing a plurality of instructions for controlling a computer system to perform an operation for biochemical data analysis, the instructions comprising:
receiving a dataset for a plurality of biological samples, the dataset having a plurality of fields for each biological sample, at least a portion of the dataset being obtained from experiments involving the biological samples, wherein the dataset includes:
a plurality of first fields, each first field including a plurality of values, each value corresponding to a respective characteristic of a respective biological sample, and
a plurality of second fields, each second field corresponding to a respective analyte and including a plurality of concentrations of the respective analyte in the experiments, each concentration corresponding to a respective biological sample;
in response to a user selecting the dataset via a graphical user interface (GUI) page of the computer system, automatically populating a drop-down box of the GUI page with the plurality of first fields, wherein the user uses an input device to select the dataset in the GUI page;
displaying, on a display of the computer system, a list of the plurality of first fields in a first region of the GUI page in response to the user selecting the drop-down box in the GUI page, wherein the user uses the input device to select the drop-down box;
receiving, at the GUI page, a selection of a compare field from the list of the plurality of first fields, wherein the user uses the input device to select the compare field;
in response to the user selecting the compare field, automatically identifying a plurality of values in the database for the selected compare field;
identifying subgroups of the biological samples in the dataset for statistical analysis based on the identified plurality of values for the selected compare field, wherein biological samples of a subgroup have a same value for the compare field;
in further response to the user selecting the dataset, automatically displaying, on the display of the computer system, a list of the plurality of second fields in a second region of the GUI page;
receiving, at the GUI page, a selection of an analyte from the list of the plurality of second fields displayed on the display of the computer system for statistical analysis, wherein the user uses the input device to select the analyte;
in response to the user selecting the analyte, retrieving a plurality of concentrations of the selected analyte from the dataset;
in response to the user selecting the analyte and the compare field, automatically displaying, on the display of the computer system, information of the retrieved plurality of concentrations separated by subgroups to convey statistical information for the selected analyte for each subgroup of the compare field, wherein the information of the retrieved plurality of concentrations separated by subgroups is displayed within a third region of the GUI page to facilitate visual comparison;
receiving, at the GUI page, a selection of a control group from a control group list, wherein the user uses the input device to select the control group; and
in response to the user selecting the control group, automatically displaying, on the display of the computer system, a visual indication as to which subgroup corresponds to the control group.

18. The computer program product of claim 17, wherein the instructions further comprise:
receiving a selection of a first filter parameter from a filter parameter list, wherein the filter parameter list includes at least a portion of the plurality of first fields, the first filter parameter having a plurality of first criteria values;
receiving a selection of a portion of the plurality of first criteria values; and
displaying statistical information corresponding to the selected portion and not to the non-selected first criteria values.

19. A computer program product comprising a tangible non-transitory computer readable medium storing a plurality of instructions for controlling a computer system to perform an operation for biochemical data analysis, the instructions comprising:
receiving a dataset for a plurality of biological samples, the dataset having a plurality of fields for each biological sample, at least a portion of the dataset being obtained from experiments involving the biological samples, wherein the dataset includes:
a plurality of first fields, each first field including a plurality of values, each value corresponding to a respective characteristic of a respective biological sample, and
a plurality of second fields, each second field corresponding to a respective analyte and including a plurality of concentrations of the respective analyte in the experiments, each concentration corresponding to a respective biological sample;
in response to a user selecting the dataset via a graphical user interface (GUI) page of the computer system, automatically populating a drop-down box of the GUI page with the plurality of first fields, wherein the user uses an input device to select the dataset in the GUI page;
displaying, on a display of the computer system, a list of the plurality of first fields in a first region of the GUI page in response to the user selecting the drop-down box in the GUI page, wherein the user uses the input device to select the drop-down box;
receiving, at the GUI page, a selection of a compare field from the list of the plurality of first fields, wherein the user uses the input device to select the compare field;
in response to the user selecting the compare field, automatically identifying a plurality of values in the database for the selected compare field;
identifying subgroups of the biological samples in the dataset for statistical analysis based on the identified plurality of values for the selected compare field, wherein biological samples of a subgroup have a same value for the compare field;
in further response to the user selecting the dataset, automatically displaying, on the display of the computer system, a list of the plurality of second fields in a second region of the GUI page;
receiving, at the GUI page, a selection of an analyte from the list of the plurality of second fields displayed on the display of the computer system for statistical analysis, wherein the user uses the input device to select the analyte;

in response to the user selecting the analyte, retrieving a plurality of concentrations of the selected analyte from the dataset;

in response to the user selecting the analyte and the compare field, automatically displaying, on the display of the computer system, information of the retrieved plurality of concentrations separated by subgroups to convey statistical information for the selected analyte for each subgroup of the compare field, wherein the information of the retrieved plurality of concentrations separated by subgroups is displayed within a third region of the GUI page to facilitate visual comparison;

receiving, at the GUI page, a selection of a first filter parameter from a filter parameter list, wherein the filter parameter list includes at least a portion of the plurality of first fields, the first filter parameter having a plurality of first criteria values;

receiving, at the GUI page, a selection of a portion of the plurality of first criteria values;

in response to the user selecting the portion, automatically displaying, on the display of the computer system, statistical information corresponding to the selected portion and not to the non-selected first criteria values;

refreshing a user view of possible criteria values based on the selected first filter parameter, wherein the possible criteria values allow filtering of data on which a statistical analysis is performed;

receiving, at the GUI page, one or more user selections of criteria values based on the refreshed user view; and in response to the user selecting the criteria values, automatically filtering the subgroups of data for statistical analysis based on the selected filtering criteria.

20. A system for biochemical data analysis comprising:
a database system; and
one or more processors configured to:
receive a dataset for a plurality of biological samples, the dataset having a plurality of fields for each biological sample, at least a portion of the dataset being obtained from experiments involving the biological samples, wherein the dataset includes:
a plurality of first fields, each first field including a plurality of values, each value corresponding to a respective characteristic of a respective biological sample, and
a plurality of second fields, each second field corresponding to a respective analyte and including a plurality of concentrations of the respective analyte in the experiments, each concentration corresponding to a respective biological sample;
in response to a user selecting the dataset via a graphical user interface (GUI) page of the computer system, automatically populate a drop-down box of the GUI page with the plurality of first fields, wherein the user uses an input device to select the dataset in the GUI page;
display, on a display of the computer system, a list of the plurality of first fields in a first region of the GUI page in response to the user selecting the drop-down box in the GUI page, wherein the user uses the input device to select the drop-down box;
receive, at the GUI page, a selection of a compare field from the list of the plurality of first fields, wherein the user uses the input device to select the compare field;
in response to the user selecting the compare field, automatically identify a plurality of values in the database for the selected compare field;
identify subgroups of the biological samples in the dataset for statistical analysis based on the identified plurality of values for the selected compare field, wherein biological samples of a subgroup have a same value for the compare field;
in further response to the user selecting the dataset, automatically display, on the display of the computer system, a list of the plurality of second fields in a second region of the GUI page;
receive, at the GUI page, a selection of an analyte from the list of the plurality of second fields displayed on the display of the computer system for statistical analysis, wherein the user uses the input device to select the analyte;
in response to the user selecting the analyte, retrieve a plurality of concentrations of the selected analyte from the dataset;
in response to the user selecting the analyte and the compare field, automatically display, on the display of the computer system, information of the retrieved plurality of concentrations separated by subgroups to convey statistical information for the selected analyte for each subgroup of the compare field, wherein the information of the retrieved plurality of concentrations separated by subgroups is displayed within a third region of the GUI page to facilitate visual comparison;
receive, at the GUI page, a selection of a control group from a control group list, wherein the user uses the input device to select the control group; and
in response to the user selecting the control group, automatically display, on the display of the computer system, a visual indication as to which subgroup corresponds to the control group.

21. The system of claim 20, wherein the one or more processors are further configured to:
receive a selection of a first filter parameter from a filter parameter list, wherein the filter parameter list includes at least a portion of the plurality of first fields, the first filter parameter having a plurality of first criteria values;
receive a selection of a portion of the plurality of first criteria values; and
display statistical information corresponding to the selected portion and not to the non-selected first criteria values.

22. A system for biochemical data analysis comprising:
a database system; and
one or more processors configured to:
receive a dataset for a plurality of biological samples, the dataset having a plurality of fields for each biological sample, at least a portion of the dataset being obtained from experiments involving the biological samples, wherein the dataset includes:
a plurality of first fields, each first field including a plurality of values, each value corresponding to a respective characteristic of a respective biological sample, and
a plurality of second fields, each second field corresponding to a respective analyte and including a plurality of concentrations of the respective analyte in the experiments, each concentration corresponding to a respective biological sample;
in response to a user selecting the dataset via a graphical user interface (GUI) page of the computer system, automatically populate a drop-down box of the GUI page with the plurality of first fields, wherein the user uses an input device to select the dataset in the GUI page;

display, on a display of the computer system, a list of the plurality of first fields in a first region of the GUI page in response to the user selecting the drop-down box in the GUI page, wherein the user uses the input device to select the drop-down box;

receive, at the GUI page, a selection of a compare field from the list of the plurality of first fields, wherein the user uses the input device to select the compare field;

in response to the user selecting the compare field, automatically identify a plurality of values in the database for the selected compare field;

identify subgroups of the biological samples in the dataset for statistical analysis based on the identified plurality of values for the selected compare field, wherein biological samples of a subgroup have a same value for the compare field;

in further response to the user selecting the dataset, automatically display, on the display of the computer system, a list of the plurality of second fields in a second region of the GUI page;

receive, at the GUI page, a selection of an analyte from the list of the plurality of second fields displayed on the display of the computer system for statistical analysis, wherein the user uses the input device to select the analyte;

in response to the user selecting the analyte, retrieve a plurality of concentrations of the selected analyte from the dataset;

in response to the user selecting the analyte and the compare field, automatically display, on the display of the computer system, information of the retrieved plurality of concentrations separated by subgroups to convey statistical information for the selected analyte for each subgroup of the compare field, wherein the information of the retrieved plurality of concentrations separated by subgroups is displayed within a third region of the GUI page to facilitate visual comparison;

receive, at the GUI page, a selection of a first filter parameter from a filter parameter list, wherein the filter parameter list includes at least a portion of the plurality of first fields, the first filter parameter having a plurality of first criteria values;

receive, at the GUI page, a selection of a portion of the plurality of first criteria values;

in response to the user selecting the portion, automatically display, on the display of the computer system, statistical information corresponding to the selected portion and not to the non-selected first criteria values;

refresh a user view of possible criteria values based on the selected first filter parameter, wherein the possible criteria values allow filtering of data on which a statistical analysis is performed;

receive, at the GUI page, one or more user selections of criteria values based on the refreshed user view; and in response to the user selecting the criteria values, automatically filter the subgroups of data for statistical analysis based on the selected filtering criteria.

* * * * *